(12) United States Patent
Cope

(10) Patent No.: US 11,497,763 B1
(45) Date of Patent: Nov. 15, 2022

(54) COMPOUNDS AND METHODS FOR TREATING AND DIAGNOSING RNA VIRUS INFECTIONS

(71) Applicant: Physis International LLC, Westerville, OH (US)

(72) Inventor: Frederick Oliver Cope, Farragut, TN (US)

(73) Assignee: Physis International LLC, Westerville, OH (US)

( * ) Notice: Subject to any disclaimer, the term of this patent is extended or adjusted under 35 U.S.C. 154(b) by 0 days.

(21) Appl. No.: 17/363,791

(22) Filed: Jun. 30, 2021

Related U.S. Application Data

(60) Provisional application No. 63/046,951, filed on Jul. 1, 2020, provisional application No. 63/158,066, filed on Mar. 8, 2021.

(51) Int. Cl.
*A61K 31/721* (2006.01)
*A61K 45/06* (2006.01)

(52) U.S. Cl.
CPC ............ *A61K 31/721* (2013.01); *A61K 45/06* (2013.01)

(58) Field of Classification Search
CPC .............................. A61K 31/721; A61K 45/06
USPC .......................................................... 514/59
See application file for complete search history.

(56) References Cited

U.S. PATENT DOCUMENTS

| | | | |
|---|---|---|---|
| 6,409,990 B1 | 6/2002 | Vera | |
| 11,007,272 B1 | 5/2021 | Cope et al. | |
| 2005/0004071 A1* | 1/2005 | Comper | A61P 31/00 514/54 |
| 2018/0099048 A1* | 4/2018 | Cope | A61K 51/0491 |

FOREIGN PATENT DOCUMENTS

WO 2016118188 A1 7/2016

OTHER PUBLICATIONS

Pence (GeroScience (2020) 42:1051-1061).*
Azad et al. (J Cytol Mol Biol. Jan. 10, 2014; 1(1), 1-10).*
Chu et al. (Chromatographia 2009, 70, September (No. 5/6), 817-824).*
Petrosillo et al. (Clinical Microbiology and Infection 26 (2020) 729-734).*
Gibney (Fierce Pharma; Jul. 7, 2015).*
Mancino et al. (Clin Cancer Res; 16(3) Feb. 1, 2010).*
Zhang et al. (Proceedings of the 106th Annual Meeting of the American Association for Cancer Research; Apr. 18-22, 2015; Philadelphia, PA. Philadelphia (PA): AACR; Cancer Res 2015;75 (15 uppl):Abstract nr 5026).*
Pfizer Limited (https://www.medicines.org.uk/emc/product/6184/smpc/print; Apr. 23, 2021).*
Azad et al. (The Journal of Immunology, 2015, 195, 1-11).*
Alsharif, W. et al., Effectiveness of COVID-19 diagnosis and management tools: A review, Radiography, 2021, pp. 682-687, 27, Elsevier Ltd. Available online Sep. 21, 2020 at https://doi.org/10.1016/j.radi.2020.09.010.
Anka, A. U. et al., Coronavirus disease 2019 (COVID-19): An overview of the immunopathology, serological diagnosis and management, Scand J Immunol. 2021, 12 pages, 93:e12998, Wiley. Available online Nov. 15, 2020 at https://doi.org/10.1111/sji.12998.
Cleanlink, SARS-CoV-2 and COVID-19: What's the Difference?, Mar. 10, 2020, 9 pages.
Cope, F. et al., The Inextricable Axis of Targeted Diagnostic Imaging and Therapy: An Immunological Natural History Approach, HHS Public Access, Nucl Med Biol. Author Manuscript, Mar. 1, 2017, 31 pages. Published in final edited form as Nucl Med Biol., Mar. 2016, pp. 215-225, 43(3). https://doi:10.1016/j.nucmedbio.2015.11.007.
Lotfi, M. et al., COVID-19: Transmission, prevention, and potential therapeutic Opportunities, Clinica Chimica Acta, 2020, pp. 254-266, 508, Elsevier B.V. Available on May 29, 2020 at https://doi.org/10.1016/j.cca.2020.05.044.
Rivett, L. et al., Screening of healthcare workers for SARS-CoV-2 highlights the role of asymptomatic carriage in COVID-19 transmission, eLife, Epidemiology and Global—Health Human Biology and Medicine, 2020, pp. 1-20, 9: e58728. Available online May 11, 2020 at https://doi.org/10.7554/eLife.58728.
Tajbakhsh, A. et al., COVID-19 and cardiac injury: clinical manifestations, biomarkers, mechanisms, diagnosis, treatment, and follow up, Expert Review of Anti-Infective Therapy, pp. 345-357, 2021, 19:3, Taylor & Francis Group. Available online Sep. 28, 2020 at https://doi.org/10.1080/14787210.2020.1822737.
Taleghani, N. et al., Diagnosis of COVID-19 for controlling the pandemic: A review of the state-of-the-art, Biosensors and Bioelectronics, 2021, pp. 1-17, 174, 112830, Elsevier B.V. Available online Nov. 27, 2020 at https://doi.org/10.1016/j.bios.2020.112830.

* cited by examiner

*Primary Examiner* — Shaojia A Jiang
*Assistant Examiner* — Michael C Henry
(74) *Attorney, Agent, or Firm* — Standley Law Group LLP; Adam Smith; Kenny Pung

(57) ABSTRACT

A compound that includes a dextran backbone having at least one C-type lectin targeting moieties attached thereto. Also disclosed are embodiments of the compound that include at least one therapeutic agent and/or at least one detection label attached to the dextran backbone. The compound may be effective for treatment of Corona Covid-19 (SARS-covid-2) virus, its variants and other related viral diseases, and disorders. Further disclosed are methods for diagnosing and treating diseases and/or disorders directly using the disclosed compounds.

Figure 1:
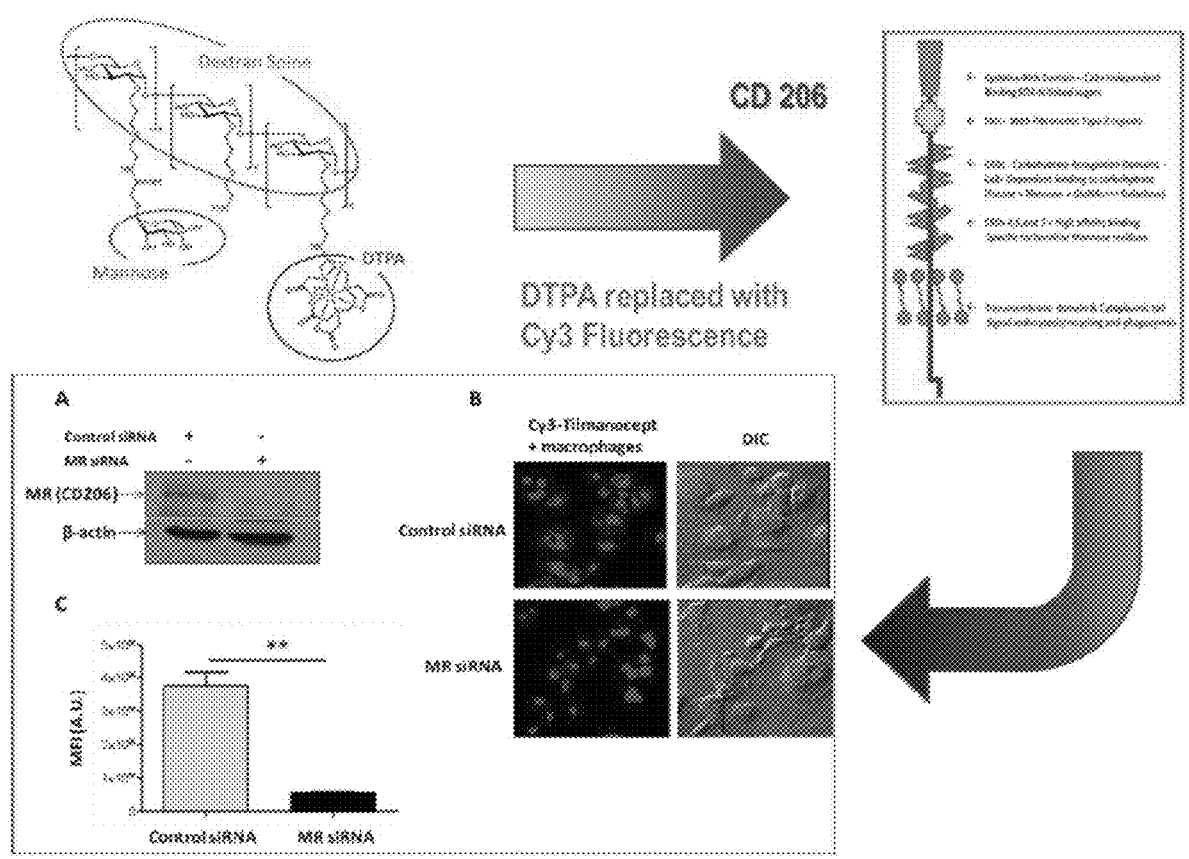

9 Claims, 13 Drawing Sheets
(13 of 13 Drawing Sheet(s) Filed in Color)

COMPOUNDS AND METHODS FOR TREATING AND DIAGNOSING RNA VIRUS INFECTIONS

CROSS-REFERENCE TO RELATED APPLICATIONS

This application claims the benefit of U.S. Provisional Application Ser. No. 63/046,951 filed Jul. 1, 2020 as well as U.S. Provisional Application Ser. No. 63/158,066 filed Mar. 8, 2021, the disclosures of each of which are hereby incorporated by reference as if fully restated herein.

TECHNICAL FIELD

Exemplary embodiments relate generally to systems and methods for treating and diagnosing RNA virus infections, and more specifically, Corona viruses and their variants.

BACKGROUND AND SUMMARY OF THE INVENTION

SARS-covid-2 disease (Covid-19) (sometimes also referred to as severe acute respiratory syndrome coronavirus 2, SARS-CoV-2 and/or COVID-19; exemplification sometimes referred to as Wuhan virus, Chinese corona virus, and/or Covid-19), can cause Covid-19 virus disease (or, at times, referred to as SARS) and is the strain of corona-virus that causes coronavirus disease 2019 (hereinafter generally referred to as "COVID-19"), a respiratory illness. Colloquially known as coronavirus, COVID-19 was previously referred to by its provisional name 2019 novel coronavirus (2019-nCoV). As described by the National Institutes of Health, COVID-19 is the successor to SARS-CoV-1. COVID-19 is a positive-sense single-stranded RNA virus. It is contagious in humans, and the World Health Organization (WHO) has designated the ongoing pandemic of COVID-19 (temporally, December, 2019 through months of 2020, and beyond) a Public Health Emergency of International Concern. Taxonomically, SARS-CoV-2 is a strain of severe acute respiratory syndrome-related coronavirus (SARSrCoV). It is believed to have zoonotic origins and has close genetic similarity to bat coronaviruses, suggesting it emerged from a bat-borne virus. The virus shows little genetic diversity, indicating that the spillover event introducing SARS-CoV-2 to humans is likely to have occurred in late 2019.

Epidemiological studies estimate each infection results in 1.4 to 3.9 new ones when no members of the community are immune and no preventive measures are taken. The virus primarily spreads between people through close contact and via respiratory droplets produced from coughs or sneezes. It mainly enters human cells by binding to the receptor angiotensin converting enzyme 2 (ACE2) of the upper respiratory tract and nares. While the Covid-19 virus has been shown to expressly enter and infect cells and human subjects via the ACE2 receptor (angiotension converting enzyme-2, ACE-2), presented herein are unexpected findings that macrophages in the lungs and liver are solely the harbingers of the Covid-19 virus and that this relationship appears to be the driving element of the disposition of the pulmonary disease as well as the disseminated involvement of other organs leading to the thrombosis cascade within the alveoli and vessels of the lungs and other larger bodily blood vessels.

While there is no known Covid-19 virus-specific treatment, the combination of hydroxychloroquine and/or azithromycin+zinc supplementation and/or Remdesivir® and/or steroids, may help with the symptoms. But these treatments are marginally adequate and are non-specific relative to the data-based targeting approach presented here, which includes a biologically more adequate address to the entirety of the infection process where key reactions of macrophages are activated pathologically, particularly in latter disease stages where in the lung, such macrophages appear to drive a thrombolytic cascade that is also diffuse (liver, bowel, and large vessels). Other prior art medications or vaccines have failed to cytologically target the ongoing Covid-19 disease process.

In January 2020, the President of the United States, in conjunction with the Centers for Disease Control and Prevention (CDC), issued travel prohibitions on affected countries, including the use of enhanced precautions. As such, needs exist to establish a way of effectively treating and/or preventing Covid-19 virus morbidity and mortality.

On Jan. 30, 2020, the World Health Organization declared a Public Health Emergency of International Concern regarding neurological disorders associated with Covid-19. At present, neither vaccination nor specific prophylactic antiviral therapies are readily available to prevent Covid-19 infections, though certain vaccinations are presently undergoing development and clinical trials, demonstrating the international need for embodiments of the inventions described herein.

Embodiments of the present invention are generally directed to compounds and compositions for targeting macrophages, which may include a dextran-based molecular entity in exemplary embodiments. The present invention also includes methods of making such compounds and compositions. The present invention also includes methods of treatment using such compounds and compositions. The present invention also provides diagnostic methods, including, but not limited to, identification of macrophages in the lungs and liver, most particularly in tissues derived from cadavers of Covid-19 victims.

CD206 is a C-type lectin protein found on macrophage phenotypes and other cells, e.g., Kupffer cells of the liver and mesangial cells of the kidney.

In one aspect, the present invention provides compounds, compositions and methods for the diagnosis and/or treatment of diseases mediated by CD206-high expressing cells using synthetic macromolecules (e.g., about 2-30 kDa). These diseases may include any condition where macrophages or other CD206-high expressing cells are involved or recruited, such as those where the number of macrophages or other CD206-high expressing cells is increased and/or such cells are metabolically abnormal, such as, but not limited to, in viral infections, tumor environments, combinations thereof, or the like. Such diseases may include immune diseases, inflammatory diseases, and infectious diseases to name a few examples.

In another aspect, the present invention provides compounds, compositions and methods for the diagnosis and/or treatment of diseases mediated by non CD206-expressing cells using synthetic macromolecules.

Disclosed includes compounds and methods for treating diseases or disorders.

In exemplary embodiments, the compound is a compound according to Formula (II):

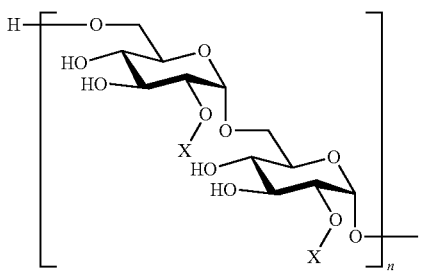

or a pharmaceutically acceptable salt thereof. X may independently comprise a hydrogen, $L_1$-A, or $L_2$-R. $L_1$ may comprise a linker. A may independently comprise a hydrogen, a therapeutic agent, or a detection label that is attached to $L_1$. $L_2$ may comprise a linker. R may independently comprise a hydrogen or a CD206 targeting moiety that is attached to $L_2$. n may comprise an integer greater than zero. The compound may include at least one $L_1$-A, such as wherein the A is a CD206 targeting moiety. The compound may further comprise at least one $L_2$-R.

In another embodiment, the compound may include a dextran backbone having at least one C-type lectin targeting moieties and at least one therapeutic agent attached thereto, wherein said compound is effective for treatment of Corona Covid-19 (SARS-covid-2) virus.

In exemplary embodiments, a method of treatment may include administering, to a subject afflicted with a disease or disorder, a compound comprising a C-type lectin targeting moiety. The method may further include delivering, to cells of the subject that comprise C-type lectin, at least one of a therapeutic agent and a detection label.

In exemplary embodiments, a method of diagnosing may include identification of macrophages in the lungs and liver.

Further features and advantages of the systems and methods disclosed herein, as well as the structure and operation of various aspects of the present disclosure, are described in detail below with reference to the accompanying figures.

BRIEF DESCRIPTION OF THE DRAWINGS

The patent or application file contains at least one drawing executed in color. Copies of this patent or patent application with color drawing(s) will be provided by the Office upon request and payment of the necessary fee. In addition to the features mentioned above, other aspects of the present invention will be readily apparent from the following descriptions of the drawings and exemplary embodiments, wherein like reference numerals across the several views refer to identical or equivalent features, and wherein:

FIG. 1 illustrates co-localization of dextran/mannose and expression of CD206 in human macrophages;

FIG. 2 illustrates COVID-19 RNA expression in lung alveolar structures in a patient deceased by COVID-19;

FIG. 3 illustrates CD11B expression in lung alveolar structures in a patient deceased by COVID-19;

FIG. 4 illustrates CD206/Covid-19 co-expression (merged) in lung alveolar structures of an 80-year-old patient deceased by COVID-19;

FIG. 5 illustrates Hematoxylin CD206/Covid-19 expression in lung alveolar macrophages of a patient deceased by COVID-19;

FIG. 6 illustrates Covid-19 RNA expression in lung alveolar macrophages (with hematoxylin co-staining, blue) in a patient deceased by COVID-19;

FIG. 7 illustrates COVID-19 RNA expression in lung alveolar structures (blue/green) of a patient deceased by COVID-19;

FIG. 8 illustrates CD206 expression in lung alveolar structures and dendritic cells (red) of a patient deceased by COVID-19;

FIG. 9 illustrates CD206/COVID-19 co-expression (merged) in lung alveolar macrophages (yellow) of a patient deceased by COVID-19;

FIG. 10 illustrates hematoxylin lung alveolar macrophages (with expression brown=Covid 19 and red=CD206) of a patient deceased by COVID-19;

FIG. 11 illustrates Covid-19 nucleocapsid expression in lung alveolar structures (blue/green) of a patient deceased by COVID-19;

FIG. 12 illustrates CD163 activated macrophage expression in lung alveolar structures (red/pink) in a patient deceased by COVID-19; and FIG. 13 illustrates merged lung alveolar macrophages with COVID-19 RNA expression in a patient deceased by COVID-19 (blue/green=nucleocapsid COVID-19, red=CD163/Activated Macrophages; NOTE: there is no expression in alveolar endothelial cells).

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein may be made without departing from the scope and spirit of the present invention. In addition, descriptions of well-known functions and constructions are omitted for clarity and conciseness.

As used herein, nomenclature for compounds, including organic compounds, may be referred to using common names, such as, but not limited to, those provided in the IUPAC, IUBMB, or CAS recommendations for nomenclature. When one or more stereochemical features are present, Cahn-Ingold-Prelog rules for stereochemistry may be employed to designate stereochemical priority, E/Z specification, and the like. One of skill in the art may readily ascertain the structure of a compound if given a name, either by systemic reduction of the compound structure using naming conventions, or by commercially available software, such as CHEMDRAW™ (available from Perkin Elmer Corporation, U.S.A.).

As used in the specification, the singular forms "a," "an" and "the" may include plural referents unless the context clearly dictates otherwise. Thus, for example, reference to "a functional group," "an alkyl," or "a residue" may include mixtures of two or more such functional groups, alkyls, or residues, and the like.

Ranges may be expressed herein as from "about" one particular value, and/or to "about" another particular value. When such a range is expressed, a further aspect may include the one particular value and/or to the other particular value. Similarly, when values are expressed as approximations, by use of the antecedent "about," it will be understood that the particular value forms a further aspect. It will be further understood that the endpoints of each of the ranges may be significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 may also be disclosed.

References in the specification to parts by weight of a particular element or component in a composition may denote the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratios regardless of whether additional components are contained in the compound.

A weight percent (wt. %) of a component may be based on the total weight of the formulation or composition in which the component is included.

As used herein, the terms "optional" or "optionally" may refer to the subsequently described event or circumstance may or may not occur, and that the description may include instances where said event or circumstance occurs and instances where it does not. The omission of "optional" or "optionally" does not necessarily mean that the subsequently described event, circumstances, or components are mandatory.

As used herein, the term "subject" may include a vertebrate, such as a mammal, a fish, a bird, a reptile, or an amphibian. Thus, the subject of the herein disclosed methods may include a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient may refer to a subject afflicted with a disease or disorder. The term "patient" may include human and veterinary subjects.

As used herein, the term "treatment" may refer to the medical management of a patient with the intent to cure, ameliorate, stabilize, or prevent a disease, pathological condition, or disorder. This term may include active treatment, e.g., treatment directed specifically toward the improvement of a disease, pathological condition, or disorder, and also may include causal treatment, e.g., treatment directed toward removal of the cause of the associated disease, pathological condition, or disorder. In addition, this term may include palliative treatment, e.g., treatment designed for the relief of symptoms rather than the curing of the disease, pathological condition, or disorder; preventative treatment, e.g., treatment directed to minimizing or partially or completely inhibiting the development of the associated disease, pathological condition, or disorder; and supportive treatment, e.g., treatment employed to supplement another specific therapy directed toward the improvement of the associated disease, pathological condition, or disorder. In various aspects, the term covers any treatment of a subject, including a mammal (e.g., a human), and may include: (i) preventing the disease from occurring in a subject that may be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also may include domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" may refer to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the terms "modulate" or "regulate" referring to cells may induce altered states of the cell or cells as this may relate to their phenotype or production of factors, e.g. IL-6, interferon, cytokines or other gene or cell product expression.

As used herein, the term "diagnosed" may include having been subjected to a physical examination by a person of skill, for example, a physician, and found to have a condition that may be diagnosed or treated by the compounds, compositions, or methods disclosed herein.

As used herein, the phrase "identified to be in need of treatment for a disorder," or the like, may refer to selection of a subject based upon need for treatment of the disorder. For example, a subject may be identified as having a need for treatment of a disorder based upon an earlier diagnosis by a person of skill and thereafter subjected to treatment for the disorder. It is contemplated that the identification can, in one aspect, be performed by a person different from the person making the diagnosis. It is also contemplated, in a further aspect, that the identification may be performed by one who subsequently performed the administration.

As used herein, the terms "administering" and "administration" refer to any method of providing a pharmaceutical preparation to a subject. Such methods are well known to those skilled in the art and may include, but are not limited to, oral administration, transdermal administration, administration by inhalation, nasal administration, topical administration, intravaginal administration, ophthalmic administration, intra-aural administration, intracerebral administration, rectal administration, sublingual administration, intradermal administration, buccal administration, and parenteral administration, including injectable such as intravenous administration, intra-arterial administration, intramuscular administration, and subcutaneous administration. Administration may be continuous or intermittent. In various aspects, a preparation may be administered therapeutically; e.g., administered to treat an existing disease or condition. In further various aspects, a preparation may be administered prophylactically; e.g., administered for prevention of a disease or condition. Combinations of administrations may be utilized.

The term "contacting" as used herein may refer to bringing a disclosed compound and a cell, a target receptor (e.g.

CD206, CD209, CD69, CD23, CLEC-2, LOX-1, MBP, NKG2D, I-selectin, Dectin-1, mincle or other C-type lectin expressed by macrophage cell types or other receptor), or other biological entity together in such a manner that the compound may affect the activity of the target, either directly; i.e., by interacting with the target itself, or indirectly; i.e., by interacting with another molecule, co-factor, factor, or protein on which the activity of the target is dependent.

CD206, CD209, CD69, CD23, CLEC-2, LOX-1, MBP, NKG2D, I-selectin, Dectin-1, and mincle are mannose binding receptors expressed on macrophages. When these macrophages co-harbor with Covid-19 and are activated, these macrophages can induce Covid-19 symptoms such as a thrombolytic cascade.

As used herein, the terms "effective amount" and "amount effective" may refer to an amount that is sufficient to achieve the desired result or to have an effect on an undesired condition. For example, a "therapeutically effective amount" may refer to an amount that is sufficient to achieve the desired therapeutic result or to have an effect on undesired symptoms, but is generally insufficient to cause unacceptable adverse side effects. The specific therapeutically effective amount (i.e., dose level) for any particular patient may depend upon a variety of factors including, but not limited to, the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed; combinations thereof; and like factors well known in the medical arts. For example, it is well within the skill of the art to start doses of a compound at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. The dosage may be adjusted by the individual physician in the event of any contraindications. Dosage may vary, and may be administered in one or more dose administrations daily, for one or several days. Guidance may be found in the literature for appropriate dosages for given classes of pharmaceutical products. In further various aspects, a preparation may be administered in a "prophylactically effective amount"; e.g., an amount effective for prevention of a disease or condition.

The term "pharmaceutically acceptable" describes a material that is not biologically or otherwise undesirable, e.g., without causing an unacceptable level of undesirable biological effects or interacting in a deleterious manner.

As used herein, the term "pharmaceutically acceptable carrier" may refer to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity may be maintained, for example, by the use of coating materials such as lecithin, and by the maintenance of the required particle size in the case of dispersions and by the use of surfactants. These compositions may also contain adjuvants such as preservatives, wetting agents, emulsifying agents and dispersing agents. Prevention of the action of microorganisms may be ensured by the inclusion of various antibacterial and antifungal agents such as paraben, chlorobutanol, phenol, sorbic acid and the like. It may additionally or alternatively be desirable to include isotonic agents such as sugars, sodium chloride and the like. Prolonged absorption of the injectable pharmaceutical form may be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release may be controlled. Depot injectable formulations are also prepared by entrapping the drug in liposomes or microemulsions which are compatible with body tissues. The injectable formulations may be sterilized, for example, by filtration through a bacterial-retaining filter or by incorporating sterilizing agents in the form of sterile solid compositions which may be dissolved or dispersed in sterile water or other sterile injectable media just prior to use. Suitable inert carriers may include sugars such as lactose. Desirably, at least 95% by weight of the particles of the active ingredient have an effective particle size in the range of 0.01 to 10 micrometers.

"Alkyl" may refer to a saturated aliphatic hydrocarbon including straight chain and branched chain groups. "Alkyl" may be exemplified by groups such as methyl, ethyl, n-propyl, isopropyl, n-butyl and the like. Alkyl groups may be substituted or unsubstituted. More than one substituent may be present. Substituents may also be themselves substituted. When substituted, the substituent group is preferably, but not limited to, $C_1$-$C_4$ alkyl, aryl, heteroaryl, amino, imino, cyano, halogen, alkoxy or hydroxyl. "$C_1$-$C_4$ alkyl" may refer to alkyl groups containing one to four carbon atoms.

"Alkenyl" may refer to an unsaturated aliphatic hydrocarbon moiety including straight chain and branched chain groups. Alkenyl moieties must contain at least one alkene. "Alkenyl" may be exemplified by groups such as ethenyl, n-propenyl, isopropenyl, n-butenyl and the like. Alkenyl groups may be substituted or unsubstituted. More than one substituent may be present. When substituted, the substituent group is preferably alkyl, halogen or alkoxy. Substituents may also be themselves substituted. Substituents may be placed on the alkene itself and also on the adjacent member atoms or the alkenyl moiety. "$C_2$-$C_4$ alkenyl" may refer to alkenyl groups containing two to four carbon atoms.

"Alkynyl" may refer to an unsaturated aliphatic hydrocarbon moiety including straight chain and branched chain groups. Alkynyl moieties must contain at least one alkyne. "Alkynyl" may be exemplified by groups such as ethynyl, propynyl, n-butynyl and the like. Alkynyl groups may be substituted or unsubstituted. More than one substituent may be present. When substituted, the substituent group is preferably alkyl, amino, cyano, halogen, alkoxyl or hydroxyl. Substituents may also be themselves substituted. Substituents are not on the alkyne itself but on the adjacent member atoms of the alkynyl moiety. "$C_2$-$C_4$ alkynyl" may refer to alkynyl groups containing two to four carbon atoms.

"Acyl" or "carbonyl" may refer to the group —C(O)R wherein R is alkyl; alkenyl; alkynyl, aryl, heteroaryl, carbocyclic, heterocarbocyclic; $C_1$-$C_4$ alkyl aryl or $C_1$-$C_4$ alkyl heteroaryl. $C_1$-$C_4$ alkylcarbonyl may refer to a group wherein the carbonyl moiety is preceded by an alkyl chain of 1-4 carbon atoms.

"Alkoxy" may refer to the group —O—R wherein R is acyl, alkyl alkenyl, alkyl alkynyl, aryl, carbocyclic; heterocarbocyclic; heteroaryl, $C_1$-$C_4$ alkyl aryl or $C_1$-$C_4$ alkyl heteroaryl.

"Amino" may refer to the group —NR'R' wherein each R' is, independently, hydrogen, amino, hydroxyl, alkoxyl, alkyl, aryl, cycloalkyl, heterocycloalkyl, heteroaryl, $C_1$-$C_4$ alkyl aryl or $C_1$-$C_4$ alkyl heteroaryl. The two R' groups may themselves be linked to form a ring. The R' groups may themselves be further substituted, in which case the group also known as guanidinyl is specifically contemplated under the term "amino".

"Aryl" ay refer to an aromatic carbocyclic group. "Aryl" may be exemplified by phenyl. The aryl group may be substituted or unsubstituted. More than one substituent may be present. Substituents may also be themselves substituted. When substituted, the substituent group is preferably but not limited to heteroaryl, acyl, carboxyl, carbonylamino, nitro, amino, cyano, halogen, or hydroxyl.

"Carboxyl" may refer to the group —C(=O)O—$C_1$-$C_4$ alkyl.

"Carbonyl" may refer to the group —C(O)R wherein each R is, independently, hydrogen, alkyl, aryl, cycloalkyl; heterocycloalkyl, heteroaryl, $C_1$-$C_4$ alkyl aryl or $C_1$-$C_4$ alkyl heteroaryl.

"Carbonylamino" may refer to the group —C(O)NR'R' wherein each R' is, independently, hydrogen, alkyl, aryl, cycloalkyl, heterocycloalkyl, heteroaryl, $C_1$-$C_4$ alkyl aryl or $C_1$-$C_4$ alkyl heteroaryl. The two R' groups may themselves be linked to form a ring.

"$C_1$-$C_4$ alkyl aryl" may refer to $C_1$-$C_4$ alkyl groups having an aryl substituent such that the aryl substituent is bonded through an alkyl group. "$C_1$-$C_4$ alkyl aryl" may be exemplified by benzyl.

"$C_1$-$C_4$ alkyl heteroaryl" may refer to $C_1$-$C_4$ alkyl groups having a heteroaryl substituent such that the heteroaryl substituent is bonded through an alkyl group.

"Carbocyclic group" or "cycloalkyl" may refer to a monovalent saturated or unsaturated hydro-carbon ring. Carbocyclic groups are monocyclic, or are fused, spiro, or bridged bicyclic ring systems. Monocyclic carbocyclic groups contain 3 to 10 carbon atoms, preferably 4 to 7 carbon atoms, and more preferably 5 to 6 carbon atoms in the ring. Bicyclic carbocyclic groups contain 8 to 12 carbon atoms, preferably 9 to 10 carbon atoms in the ring. Carbocyclic groups may be substituted or unsubstituted. More than one substituent may be present. Substituents may also be themselves substituted. Preferred carbocyclic groups include cyclopropyl, cyclobutyl, cyclopentyl, cyclohexyl, cyclohexenyl, and cycloheptyl. More preferred carbocyclic groups include cyclopropyl and cyclo-butyl. The most preferred carbocyclic group is cyclopropyl. Carbocyclic groups may be not aromatic.

"Halogen" may refer to fluoro, chloro, bromo or iodo moieties. Preferably, the halogen is fluoro, chloro, or bromo.

"Heteroaryl" or "heteroaromatic" may refer to a monocyclic or bicyclic aromatic carbocyclic radical having one or more heteroatoms in the carbocyclic ring. Heteroaryl may be substituted or unsubstituted. More than one substituent may be present. When substituted, the substituents may themselves be substituted. Preferred but non limiting substituents are aryl, $C_1$-$C_4$ alkylaryl, amino, halogen, hydroxy, cyano, nitro, carboxyl, carbonylamino, or $C_1$-$C_4$ alkyl. Preferred heteroaromatic groups include tetrazoyl, triazolyl, thienyl, thiazolyl, purinyl, pyrimidyl, pyridyl, and furanyl. More preferred heteroaromatic groups include benzothiofuranyl; thienyl, furanyl, tetrazoyl, triazolyl, and pyridyl.

"Heteroatom" may refer to an atom other than carbon in the ring of a heterocyclic group or a heteroaromatic group or the chain of a heterogeneous group. Preferably, heteroatoms are selected from the group consisting of nitrogen, sulfur, and oxygen atoms. Groups containing more than one heteroatom may contain different heteroatoms.

"Heterocarbocyclic group" or "heterocycloalkyl" or "heterocyclic" may refer to a monovalent saturated or unsaturated hydrocarbon ring containing at least one heteroatom. Heterocarbocyclic groups are monocyclic, or are fused, spiro, or bridged bicyclic ring systems. Monocyclic heterocarbocyclic groups contain 3 to 10 carbon atoms, preferably 4 to 7 carbon atoms, and more prefer-ably 5 to 6 carbon atoms in the ring. Bicyclic heterocarbocyclic groups contain 8 to 12 carbon at-oms, preferably 9 to 10 carbon atoms in the ring. Heterocarbocyclic groups may be substituted or unsubstituted. More than one substituent may be present. Substituents may also be themselves substituted. Preferred heterocarbocyclic groups include epoxy, tetrahydrofuranyl, azacyclopentyl, azacyclohexyl, piperidyl, and homopiperidyl. More preferred heterocarbocyclic groups include piperidyl, and homopiperidyl. The most preferred heterocarbocyclic group is piperidyl. Heterocarbocyclic groups may be not aromatic.

"Hydroxy" or "hydroxyl" may refer to a chemical entity that consists of —OH. Alcohols contain hydroxy groups. Hydroxy groups may be free or protected. An alternative name for hydroxy is hydroxyl.

"Member atom" may refer to a carbon, nitrogen, oxygen or sulfur atom. Member atoms may be substituted up to their normal valence. If substitution is not specified, the substituents required for valency are hydrogen.

"Ring" may refer to a collection of member atoms that are cyclic. Rings may be carbocyclic, aromatic, or heterocyclic or heteroaromatic, and may be substituted or unsubstituted, and may be saturated or unsaturated. More than one substituent may be present. Ring junctions with the main chain may be fused or spirocyclic. Rings may be monocyclic or bicyclic. Rings contain at least 3 member atoms and at most 10 member atoms. Monocyclic rings may contain 3 to 7 member atoms and bicyclic rings may contain from 8 to 12 member atoms. Bicyclic rings themselves may be fused or spirocyclic.

"Thioalkyl" may refer to the group —S-alkyl.

"Tilmanocept" may refer to a non-radiolabeled precursor of the LYMPHOSEEK® diagnostic agent. Tilmanocept may be a mannosylaminodextran. It may have a dextran backbone to which a plurality of amino-terminated linkers (—O(CH2)3S(CH2)2NH2) are attached to the core glucose elements. In addition, mannose moieties may be conjugated to amino groups of a number of the linkers, and the chelator diethylenetriamine pentaacetic acid (DTPA) may be conjugated to the amino group of other linkers not containing the mannose. Tilmanocept generally, has a dextran backbone, in which a plurality of the glucose residues comprises an amino-terminated linker:

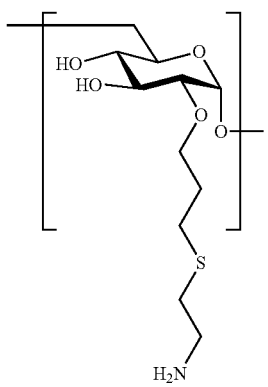

The mannose moieties may be conjugated to the amino groups of the linker via an amidine linker:

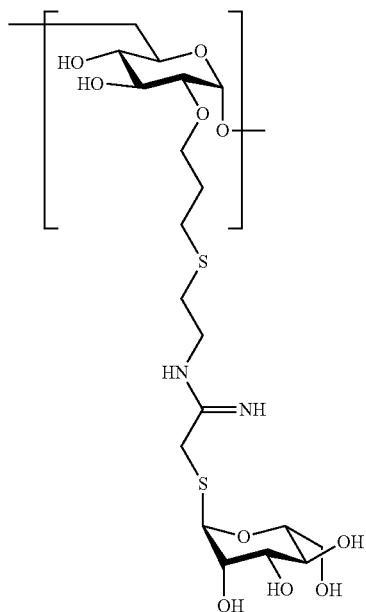

The chelator diethylenetriamine pentaacetic acid (DTPA) may be conjugated to the amino groups of the linker via an amide linker:

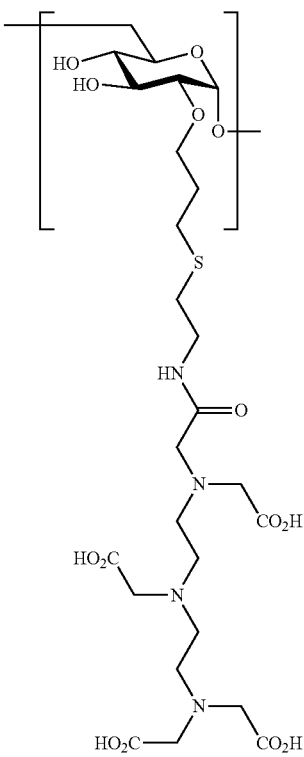

As described in the prescribing information approved for LYMPHOSEEK® in the United States, tilmanocept has the chemical name dextran 3-[(2-aminoethyl)thio] propyl 17-carboxy-10,13,16-tris(carboxymethyl)-8-oxo-4-thia-7,10,13,16-tetraazahepta-dec-1-yl 3-[[2-[[1-imino-2-(D-mannopyranosylthio)ethyl]amino]ethyl]thio] propyl ether complexes, has the following molecular formula: $[C_6H_{10}O_5]_n \cdot (C_{19}H_{28}N_4O_9S^{99m}Tc)_b \cdot (C_{13}H_{24}N_2O_5S_2)_c \cdot (C_5H_{11}NS)_a$, and contains 3-8 conjugated DTPA molecules; 12-20 conjugated mannose molecules; and 0-17 amine side chains remaining free. Tilmanocept has the following general structure:

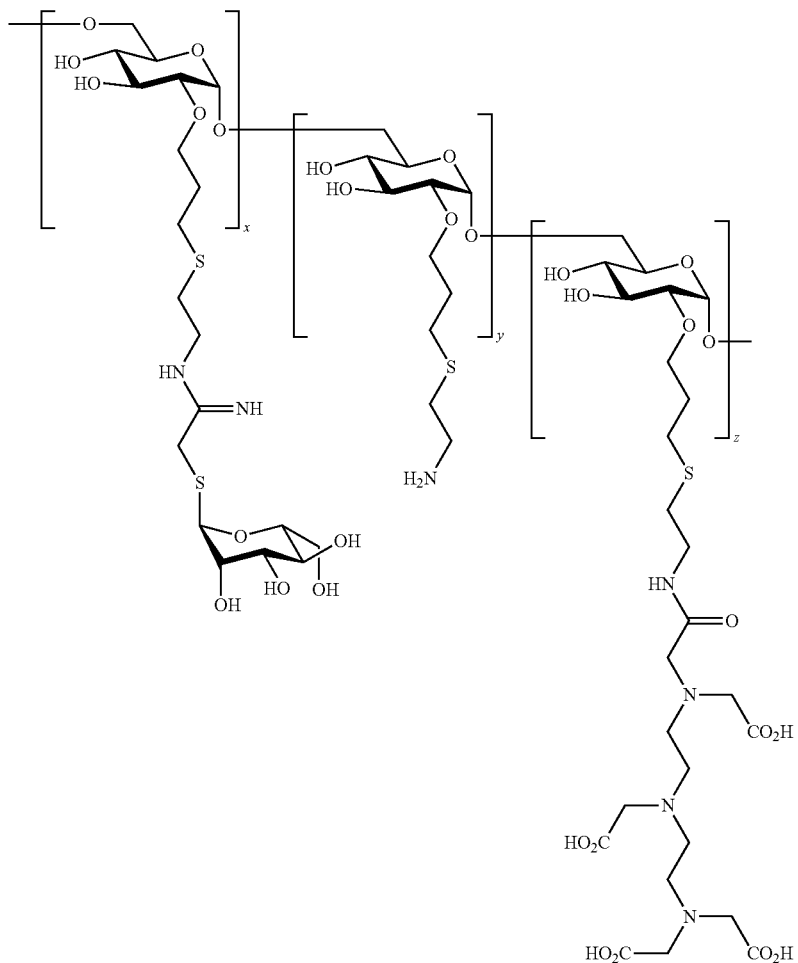

Certain of the glucose moieties may have no attached amino-terminated linker.

"Sulfonyl" may refer to the —S(O)$_2$R' group wherein R' is alkoxy, alkyl, aryl, carbocyclic, heterocarbocyclic; heteroaryl, $C_1$-$C_4$ alkyl aryl or $C_1$-$C_4$ alkyl heteroaryl.

"Sulfonylamino" may refer to the —S(O)$_2$NR'R' group wherein each R' is independently alkyl, aryl, heteroaryl, $C_1$-$C_4$ alkyl aryl or $C_1$-$C_4$ alkyl heteroaryl.

Compounds described herein may contain one or more double bonds and, thus, potentially give rise to cis/trans (E/Z) isomers, as well as other conformational isomers. Unless stated to the contrary, the invention may include all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein may contain one or more asymmetric centers and, thus, potentially give rise to diastereomers and optical isomers. The present invention may include all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures may be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer may also be referred to as an enantiomer, and a mixture of such isomers is often called an enantiomeric mixture. A 50:50 mixture of enantiomers is referred to as a racemic mixture. Many of the compounds described herein may have one or more chiral centers and therefore may exist in different enantiomeric forms. If desired, a chiral carbon may be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon may be depicted as a wedge (bonds to atoms above the plane) and the other may be depicted as a series or wedge of short parallel lines is (bonds to atoms below the plane). The Cahn-Inglod-Prelog system may be used to assign the (R) or (S) configuration to a chiral carbon.

Compounds described herein comprise atoms in both their natural isotopic abundance and in non-natural abundance. The disclosed compounds may be isotopically-labeled or isotopically-substituted compounds identical to those described, but for the fact that one or more atoms may be replaced by an atom having an atomic mass or mass number different from the atomic mass or mass number typically found in nature. Examples of isotopes that may be incorporated into compounds of the invention include isotopes of hydrogen, carbon, nitrogen, oxygen, sulfur, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C may be incorporated, are useful in drug and/or substrate tissue distribution assays. Tritiated, i.e., $^3$H, and carbon-14, i.e., $^{14}$C, isotopes may be used for their ease of preparation and detectability. Further, substitution with heavier isotopes such as deuterium, i.e., $^2$H, may afford certain therapeutic advantages resulting from greater metabolic stability, for example increased in vivo half-life or reduced dosage requirements and, hence, may be preferred in some circumstances. Isotopically labeled compounds of the present invention and prodrugs thereof may generally be prepared by carrying out the procedures below, by substituting a readily available isotopically labeled reagent for a non-isotopically labeled reagent.

It is known that chemical substances form solids which are present in different states of order which are termed polymorphic forms or modifications. The different modifications of a polymorphic substance may differ greatly in their physical properties. The compounds according to the invention may be present in different polymorphic forms, with it being possible for particular modifications to be metastable. Unless stated to the contrary, the invention may include all such possible polymorphic forms.

Certain materials, compounds, compositions, and components disclosed herein may be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental Volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that may be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that may be performed it is understood that each of these additional steps may be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that may perform the same function that are related to the disclosed structures, and that these structures will typically achieve the same result.

Compounds

Embodiments of the present invention may employ a carrier molecule, either as the sole molecular entity or as part of a compound, that may be used in the treatment or modulation of cells. This carrier molecule (i.e., construct) may comprise a polymeric (e.g., carbohydrate) backbone and CD206 targeting moieties (e.g., mannose) conjugated thereto which enable the carrier molecule to deliver one or more active pharmaceutical ingredients to the targeted cells. An example of a suitable carrier molecule may include, for example, but without limitation, mannosylamino dextrans (MAD), which may comprise a dextran backbone comprising glucose residues. Mannose molecules and active pharmaceutical ingredients may be conjugated to some or all of the glucose residues. Specific examples of MADs include, but are not necessarily limited to, tilmanocept and m-tilmanocept (which is a derivative of tilmanocept that does not contain DTPA.

In some embodiments, the present invention may provide a compound comprising a dextran-based moiety or backbone having one or more CD206 targeting moieties and one or more therapeutic agents attached thereto. Additionally, or alternatively, the dextran-based moiety or backbone may be a monomolecular entity without a secondary therapeutic agent. The dextran-based moiety may generally comprise a dextran backbone the same or similar to that described in U.S. Pat. No. 6,409,990 issued Jun. 25, 2002 (the '990 patent), which is incorporated herein by reference. Thus, the backbone may comprise a plurality of glucose moieties (i.e., residues) primarily linked by α-1,6 glycosidic bonds. Other linkages such as α-1,4 and/or α-1,3 bonds may also be present. In some embodiments, not every backbone moiety is substituted. The CD206 targeting moieties may be attached to between about 10% and about 50% of the glucose residues of the dextran backbone, or between about 20% and about 45% of the glucose residues, or between about 25% and about 40% of the glucose residues. In some embodiments, the dextran-based moiety may range from about 50 kDa to about 100 kDa, such as at least about 50 kDa, at least about 60 kDa, at least about 70 kDa, at least about 80 kDa, or at least about 90 kDa. In other exemplary embodiments, the dextran-based moiety may be less than about 100 kDa, less than about 90 kDa, less than about 80 kDa, less than about 70 kDa, or less than about 60 kDa. In yet other embodiments, the dextran backbone has a molecular weight (MW) of between about 1 kDa and about 50 kDa, while in other embodiments the dextran backbone may have a MW of between about 5 kDa and about 25 kDa. In still other exemplary embodiments, the dextran backbone may have a MW of between about 8 kDa and about 15 kDa, such as about 10 kDa. While in other exemplary embodiments the dextran backbone may have a MW of between about 1 kDa and about 5 kDa, such as about 2 kDa.

As a general rule of molecular transmembrane transport, it is well recognized that carrier molecules having smaller MW dextran backbones may be appropriate for instances where the molecule is desired to cross the blood-brain barrier, or when reduced residence time is desired (i.e., the duration of binding to CD206 is reduced). This principal may be independent of characteristics such as the charge of the molecule, tertiary folding anomalies, reaction affinities, or other molecular-specific characteristics. Carrier molecules having larger MW dextran backbones may be appropriate for instances where increased residence time is desired (i.e., the duration of binding to CD206 is increased). In certain embodiments, carrier molecules having smaller MW dextran backbones (e.g., about 1 kDa to about 5 kDa) may be employed when more efficient receptor substrates are attached to the dextran backbone (e.g., branched mannose moieties, as described below). More efficient receptor substrates may bind to CD206 for longer durations and/or more effectively, thus allowing for the use of smaller dextran backbones.

In some embodiments, the CD206 targeting moiety is selected from, but not limited to, mannose, fucose, and n-acetylglucosamine. In some embodiments, the targeting moieties are attached to between about 10% and about 50% of the glucose residues of the dextran backbone, or between about 20% and about 45% of the glucose residues, or between about 25% and about 40% of the glucose residues. It should be noted that the MWs referenced herein, as well as the number and degree of conjugation of receptor substrates, linkers, and diagnostic/therapeutic moieties attached to the dextran backbone may refer to average amounts for a given quantity of carrier molecules, since the synthesis techniques will result in some variability.

In some embodiments, linkers may be employed to facilitate the attachment of one or more CD206 targeting moieties, therapeutic agents (or drugs), and/or detection labels to the dextran-based moiety. Different linkers may be employed to varying extents depending on the desired end composition. For example, the linker may be provided on about 50% to about 100% of the backbone moieties, or on about 70% to about 90% of the backbone moieties. Branched or unbranched linkers may be employed. The linker may be an amino-terminated linker, or a linker that comprises, for example —O(CH$_2$)$_3$S(CH$_2$)$_2$NH—. If a straight chain linker is employed, the chain may range from about 1 member atoms to about 20 member atoms, and the member atoms may be selected from carbon, oxygen, sulfur, nitrogen and phosphorus. The linker may also comprise one or more substituents including, but not limited to, halo groups, perfluoroalkyl groups, perfluoroalkoxy groups, alkyl groups, such C$_{1-4}$ alkyl, alkenyl groups, such as C$_{1-4}$ alkenyl, alkynyl groups, such as C$_{1-4}$ alkynyl, hydroxy groups, oxo groups, mercapto groups, alkylthio groups, alkoxy groups, nitro groups, azidealkyl groups, aryl or heteroaryl groups, aryloxy or heteroaryloxy groups, aralkyl or heteroaralkyl groups, aralkoxy or heteroaralkoxy groups, HO—(C═O)— groups, heterocylic groups, cycloalkyl groups, amino groups, alkyl- and dialkylamino groups, carbamoyl groups, alkylcarbonyl groups, alkylcarbonyloxy groups, alkoxycarbonyl groups, alkylaminocarbonyl groups, dialkylamino carbonyl groups, arylcarbonyl groups, aryloxycarbonyl groups, alkyl sulfonyl groups, arylsulfonyl groups, —NH—NH$_2$; ═N—H; ═N-alkyl; —SH; —S-alkyl; —NH—C(O)—; —NH—C(═N)— and the like. Other suitable linkers would be known to one of ordinary skill in the art.

In some embodiments, the one or more therapeutic agent may be attached to the dextran-based moiety by way of a biodegradable linker. A biodegradable linker may be provided either in addition to, or as an alternative for, a non-biodegradable linker. A biodegradable linker such as hydrazine, which is an acid sensitive moiety, may be preferred. As those skilled in the art will appreciate, an acid sensitive linker may enable the drug to be transported into the cell and released substantially inside of the cell.

Various other linkers known to those skilled in the art or subsequently discovered may be used in place of (or in addition to) —O(CH$_2$)$_3$S(CH$_2$)$_2$NH$_2$. These include, for example, bifunctional linker groups such as alkylene diamines (H$_2$N—(CH$_2$)$_r$—NH$_2$), where r is from 2 to 12; aminoalcohols (HO—(CH$_2$)$_r$—NH$_2$), where r is from 2 to 12; aminothiols (HS—(CH$_2$)$_r$—NH$_2$), where r is from 2 to 12; amino acids that are optionally carboxy-protected; ethylene and polyethylene glycols (H—(O—CH$_2$—CH$_2$)$_n$—OH, where n is 1-4). Suitable bifunctional diamines include ethylenediamine, 1,3-propanediamine, 1,4-butanediamine, spermidine, 2,4-diaminobutyric acid, lysine, 3,3'-diaminodipropylamine, diaminopropionic acid, N-(2-aminoethyl)-1,3-propanediamine, 2-(4-aminophenyl)ethylamine, and similar compounds. One or more amino acids also may be employed as the bifunctional linker molecule, such as β-alanine, γ-aminobutyric acid or cysteine, or an oligopeptide, such as di- or tri-alanine.

Other bifunctional linkers may include:
—NH—(CH$_2$)$_r$—NH—, where r is from 2-5,
—O—(CH$_2$)$_r$—NH—, where r is from 2-5,
—NH—CH$_2$—C(O)—, —O—CH$_2$—CH$_2$—O—CH$_2$—CH$_2$—O—,
—NH—NH—C(O)—CH$_2$—,
—NH—C(CH$_3$)$_2$C(O)—,
—S—(CH$_2$)$_r$—C(O)—, where r is from 1-5,
—S—(CH$_2$)$_r$—NH—, where r is from 2-5,
—S—(CH$_2$)$_r$—O—, where r is from 1-5,
—S—(CH$_2$)—CH(NH$_2$)—C(O)—,
—S—(CH$_2$)—CH(COOH)—NH—,
—O—CH$_2$—CH(OH)—CH$_2$—S—CH(CO$_2$H)—NH—,
—O—CH$_2$—CH(OH)—CH$_2$—S—CH(NH$_2$)—C(O)—,
—O—CH$_2$—CH(OH)—CH$_2$—S—CH$_2$—CH$_2$—NH—,
—S—CH$_2$—C(O)—NH—CH$_2$—CH$_2$—NH—, and
—NH—O—C(O)—CH$_2$—CH$_2$—O—P(O$_2$H)—.

The therapeutic agent may include any compound known to be useful for the treatment of a disease vectored by biting insects.

Therapeutic agents may include, but are not limited to, chemotherapeutic agents, such as doxorubicin; drugs with effect on leishmaniasis; anti-infective agents, such as antibiotics (e.g. tetracycline, streptomycin, amphotericin and isoniazid), heavy metals such as antimony (e.g. pentavalent antimonials), anti-virals, anti-fungals, and anti-parasitics; immunological adjuvants; steroids; nucleotides, such as DNA, RNA, RNAi, siRNA, CpG or Poly (I:C); peptides; proteins; or metals such as silver, gallium or gadolinium, paromomycin, miltefosine, fluconazole, pentamide, Meglumine antimoniate, and combinations thereof.

In certain embodiments, the therapeutic agent is an anti-microbial drug selected from the group comprising: an antibiotic; an anti-tuberculosis antibiotic (such as isoniazid, streptamycin, or ethambutol); drugs which effect Corona viruses and other RNA viruses; an anti-viral or anti-retroviral drug, for example, an inhibitor of reverse transcription (such as zidovudin) or a protease inhibitor (such as indinavir). In certain embodiments, the therapeutic agent is an anti-microbial active, such as amoxicillin, ampicillin, tetracyclines, aminoglycosides (e.g., streptomycin), macrolides (e.g., erythromycin and its relatives), chloramphenicol, ivermectin, rifamycins and polypeptide antibiotics (e.g., polymyxin, bacitracin) and zwittermicin. In certain embodiments, the therapeutic agent is selected from isoniazid, doxorubicin, streptomycin, and tetracycline.

Therapeutic agents may include, but are not limited to, one or more of hydroxychloroquine, azithromycin, zinc supplementation, and Remdesivir.

In some embodiments, the therapeutic agent comprises a high energy killing isotope which has the ability to kill macrophages and tissue in the surrounding macrophage environment. Suitable radioisotopes include: $^{210/212/213/214}$Bi, $^{131/140}$Ba, $^{11/14}$C, $^{51}$Cr, $^{67/68}$Ga, $^{153}$Gd, $^{99m}$Tc, $^{88/90/91}$Y, $^{123/124/125/131}$I, $^{111/115m}$In, $^{18}$F, $^{105}$Rh, $^{153}$Sm, $^{67}$Cu, $^{166}$Ho, $^{177}$Lu, $^{186/188}$Re, $^{32/33}$P, $^{46/47}$Sc, $^{72/75}$Se, $^{35}$S, $^{182}$Ta, $^{123m/127/129/132}$Te, $^{65}$Zn and $^{89/95}$Zr.

In other embodiments, the therapeutic agent comprises a non-radioactive species selected from, but not limited to, the group consisting of: Bi, Ba, Mg, Ni, Au, Ag, V, Co, Pt, W, Ti, Al, Si, Os, Sn, Br, Mn, Mo, Li, Sb, F, Cr, Ga, Gd, I, Rh, Cu, Fe, P, Se, S, Zn and Zr, where these are primarily divalent cations.

In still further embodiments, the therapeutic agent is selected from the group consisting of modulating agents, antivirals, cytostatic agents, cytocidal agents alkylating agents, antimetabolites, anti-proliferative agents, tubulin binding agents, hormones and hormone antagonists, anthracycline drugs, vinca drugs, mitomycins, bleomycins, cytotoxic nucleosides, pteridine drugs, diynenes, podophyllotoxins, toxic enzymes, and radiosensitizing drugs. By way of more specific example, the therapeutic agent is selected from the group consisting of mechlorethamine, triethylenephosphoramide, cyclophosphamide, ifosfamide, chlorambucil, busulfan, melphalan, triaziquone, nitrosourea compounds, adriamycin, carminomycin, daunorubicin (daunomycin), doxorubicin, isoniazid, indomethacin, gallium(III), 68gallium(III), aminopterin, methotrexate, methopterin, mithramycin, streptonigrin, dichloromethotrexate, mitomycin C, actinomycin-D, porfiromycin, 5-fluorouracil, floxuridine, ftorafur, 6-mercaptopurine, cytarabine, cytosine arabinoside, podophyllotoxin, etoposide, etoposide phosphate, melphalan, vinblastine, vincristine, leurosidine, vindesine, leurosine, taxol, taxane, cytochalasin B, gramicidin D, ethidium bromide, emetine, tenoposide, colchicin, dihydroxy anthracin dione, mitoxantrone, procaine, tetracaine, lidocaine, propranolol, puromycin, ricin subunit A, abrin, diptheria toxin, botulinum, cyanginosins, saxitoxin, shigatoxin, tetanus, tetrodotoxin, trichothecene, verrucologen, corticosteroids, progestins, estrogens, antiestrogens, androgens, aromatase inhibitors, calicheamicin, hydroxychloroquine (or analogs), remdesivir (or analogs) esperamicins, and dynemicins.

In embodiments wherein the therapeutic agent is a hormone or hormone antagonist, the therapeutic agent may be selected from the group consisting of prednisone, hydroxyprogesterone, medroprogesterone, diethylstilbestrol, tamoxifen, testosterone, and aminogluthetimide.

In embodiments wherein the therapeutic agent is a prodrug, the therapeutic agent may be selected from the group consisting of phosphate-containing prodrugs, thiophosphate-containing prodrugs, sulfate containing prodrugs, peptide containing prodrugs, (-lactam-containing prodrugs, optionally substituted phenoxyacetamide-containing prodrugs, optionally substituted phenylacetamide-containing prodrugs, 5-fluorocytosinem, and 5-fluorouridine prodrugs that may be converted to the more active cytotoxic free drug.

Examples of carrier molecules (i.e., constructs) that may be useful in the present invention, either alone or in combination with the aforementioned moieties, include mannosylamino dextrans (MAD) such as tilmanocept and m-tilmanocept. In some embodiments, the dextran-based moiety having at least one CD206 targeting moiety attached thereto may be a compound of Formula (I):

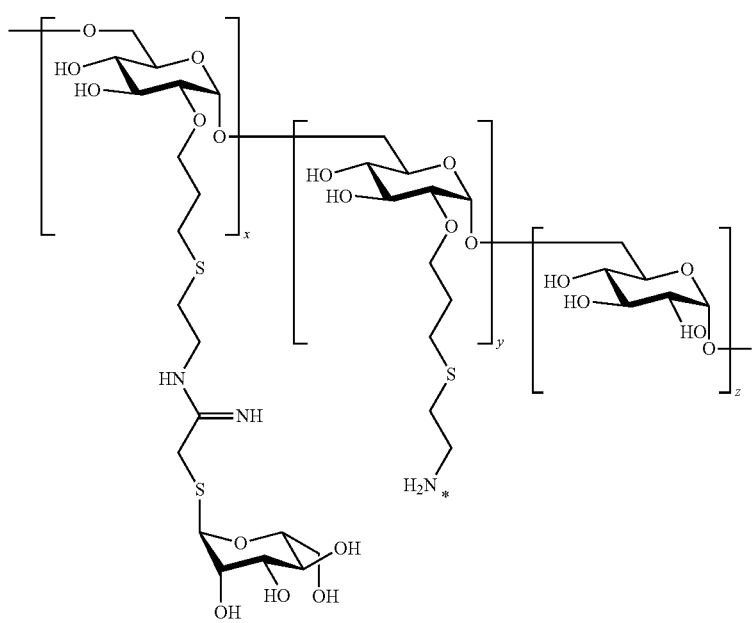

Formula (I)

The * indicates the point at which the therapeutic agent is attached. In certain embodiments, the therapeutic agent may be attached via a linker.

In other embodiments, the compound of the present invention may be a compound of Formula (II):

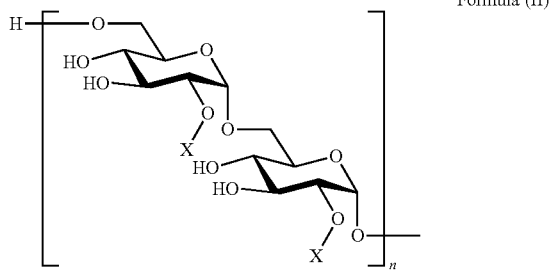

Formula (II)

Each X may independently comprise H (hydrogen), $L_1$-A, or $L_2$-R. Each $L_1$ and $L_2$ may independently comprise linkers. Each A may independently comprise a therapeutic agent or a detection label or H. Each R may independently comprise a CD206 targeting moiety or H. n may be an integer greater than zero.

In certain embodiments, $L_1$ is a linker as described above. In certain embodiments, $L_2$ is a linker as described above.

Synthesis

The compounds of this invention may be prepared by employing reactions as shown in the disclosed schemes, in addition to other standard manipulations that are known in the literature, exemplified in the experimental sections or clear to one skilled in the art. The following examples are provided so that the invention might be more fully understood, are illustrative only, and should not be construed as limiting. For clarity, examples having fewer substituents may be shown where multiple substituents are allowed under the definitions disclosed herein.

It is contemplated that each disclosed method may further comprise additional steps, manipulations, and/or components. It is also contemplated that any one or more step, manipulation, and/or component may be optionally omitted from the invention. It is understood that a disclosed method may be used to provide the disclosed compounds. It is also understood that the products of the disclosed methods may be employed in the disclosed compositions, kits, and uses.

The compounds of the present invention may be synthesized by any number of ways known to one of ordinary skill in the art. Referring to Scheme 1, for example, linker 2 may be synthesized by initiating a ring opening reaction of succinic anhydride with tert-butyl carbazate. The resulting intermediary comprises a carboxyl end group and a tert-Butyloxycarbonyl end group (for protection). The carboxyl may then be activated by EDC coupling reagent to form an ester linkage with N-hydroxy succinimide (NHS), yielding linker 2. Linker 2 may then be functionalized onto MAD (e.g., 1-3 of Scheme 1) through an amide linkage by replacing NHS. Then, the Boc protecting group may be removed under dilute acidic condition (typically 30-40% trifluoroacetic acid in DMSO) to obtain 4. Dilute acidic condition may be required to avoid any unwanted cleavage of the glycosidic linkage present in dextran backbone. The resulting functionalized MAD may be purified by size exclusion filtration.

Scheme 1: Synthetic route A for the modification of MAD.

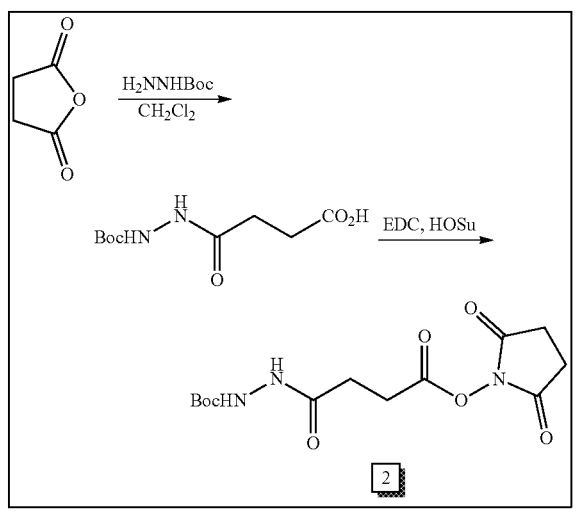

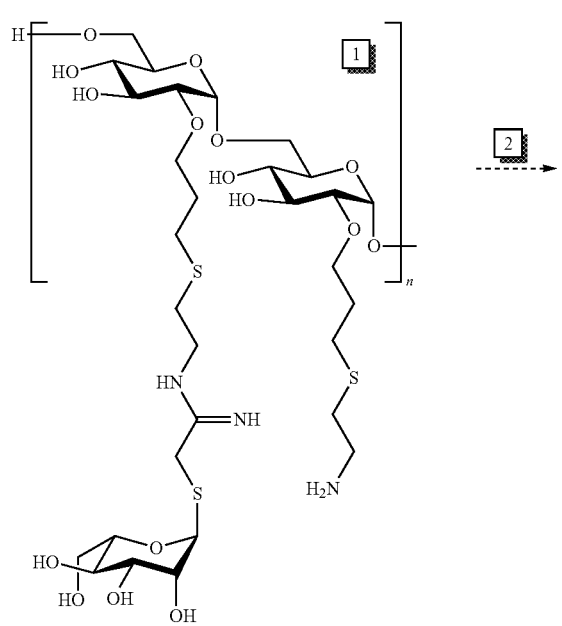

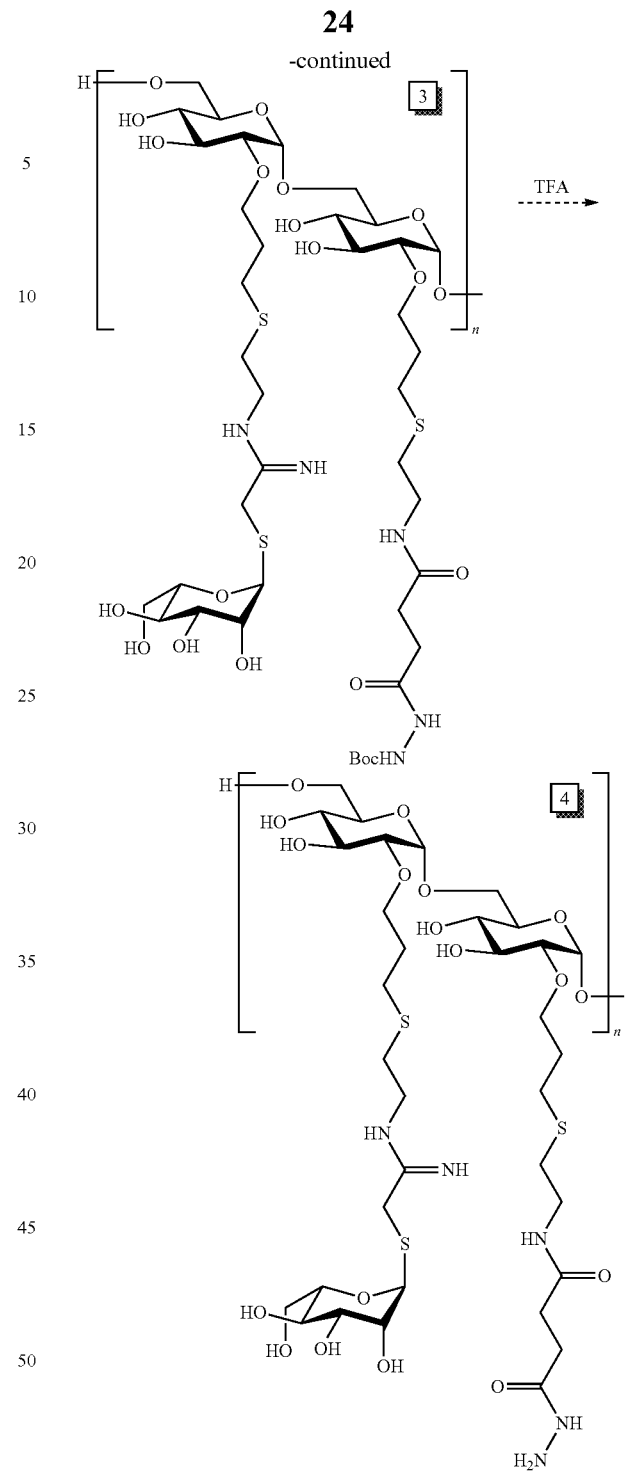

Alternatively, compounds according to the present invention may be synthesized according to Scheme 2. Referring to which, as shown below, the free primary amine groups of MAD may be reacted with an excess of lactone under anhydrous conditions, thereby opening lactone rings and forming amide linkages therebetween. Unreacted lactone may be removed under reduced pressure to obtain modified MAD 6. The corresponding hydrazine derivative 7 may be prepared by reductive amination reaction using sodium cyanoborohydride or sodium triacetoxy borohydride as the reducing agent. The resulting linker terminates in a diimide end group that may be suitable for the attachment of therapeutic agents, detection labels, and the like.

Scheme 2: Synthetic route B for the modification of MAD.

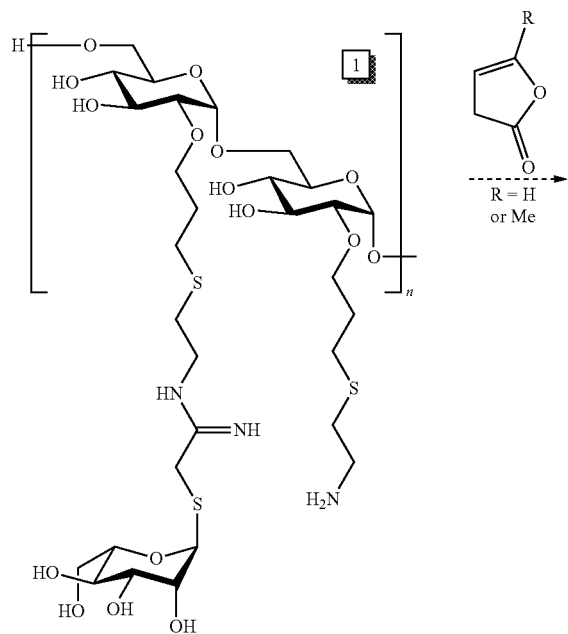

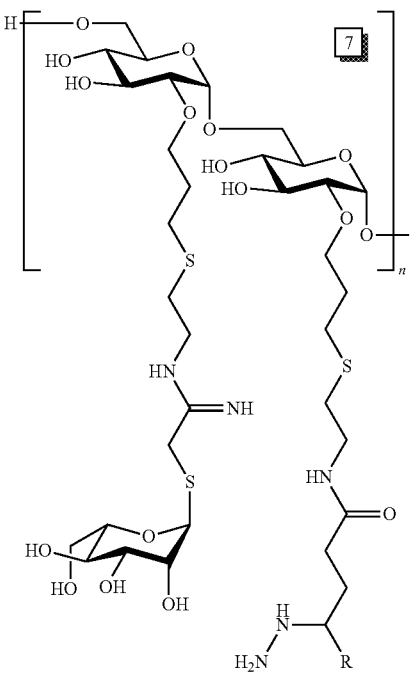

The conjugation of oxo-containing therapeutic agents to MAD derivatives 4 or 7 may be performed as shown in Scheme 3. MAD derivative 4 or 7 may be conjugated to doxorubicin via the diimide end group by the formation of a hydrazone linkage under anhydrous acidic condition or aqueous acidic conditions. Unconjugated therapeutic agent may be removed (e.g. by size exclusion chromatography or dialyzation) to obtain the pure conjugated MAD (indicated as m-tilmanocept in the scheme below).

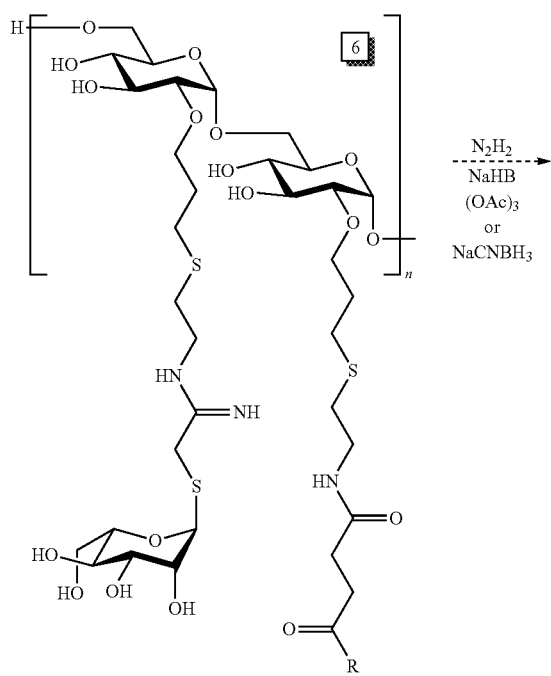

Scheme 3: Conjugation of doxorubicin to MAD derivatives.

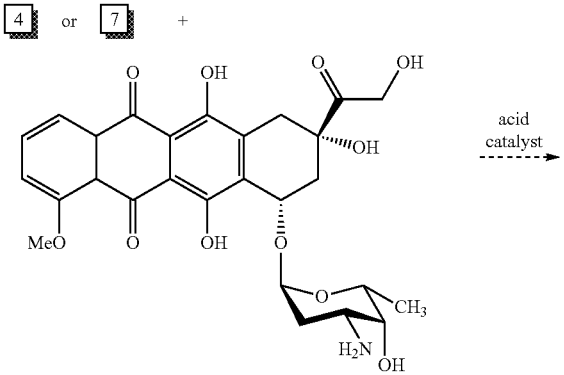

-continued

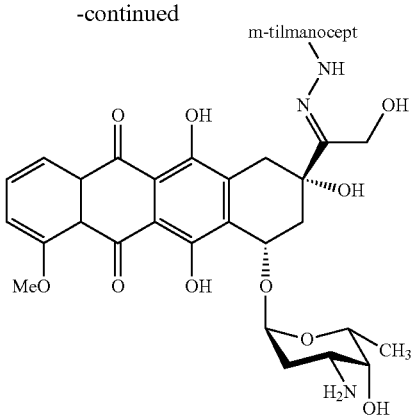
m-tilmanocept

Amine-containing therapeutic agents may be conjugated to dextran-containing compounds according to Scheme 4. The basic reaction between a primary amine and the lactone are shown in Scheme 4.

Scheme 4: Conjugation of Amine-containing therapeutic agents.

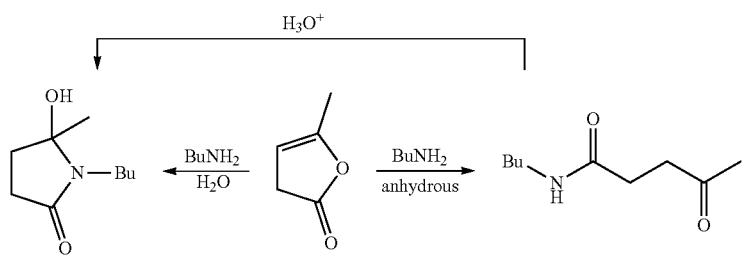

Pharmaceutical Compositions

In one aspect, the invention relates to pharmaceutical compositions comprising the disclosed compounds and products of disclosed methods. For example, without limitation, a pharmaceutical composition (i.e., a treatment dose) may be provided comprising an effective amount of at least one disclosed compound, at least one product of a disclosed method, or a pharmaceutically acceptable salt, solvate, hydrate, or polymorph thereof, and a pharmaceutically acceptable carrier. In one aspect, the invention relates to pharmaceutical compositions comprising a pharmaceutically acceptable carrier and an effective amount of at least one disclosed compound; or a pharmaceutically acceptable salt, hydrate, solvate, or polymorph thereof.

In a further aspect, the effective amount is a therapeutically effective amount. In a still further aspect, the effective amount is a prophylactically effective amount. In a still further aspect, the pharmaceutical composition comprises a compound that is a product of a disclosed method of making.

In a further aspect, the pharmaceutical composition comprises a disclosed compound. In a yet further aspect, the pharmaceutical composition comprises a product of a disclosed method of making.

In one aspect, the pharmaceutical composition is used to treat a mammal. In a yet further aspect, the mammal is a human. In a further aspect, the mammal has been diagnosed with a need for treatment of the disorder prior to the administering step. In a further aspect, the mammal has been identified to be in need of treatment of the disorder.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, intradermal and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

As used herein, the term "pharmaceutically acceptable salts" may refer to salts prepared from pharmaceutically acceptable non-toxic bases or acids. When the compound of the present invention is acidic, its corresponding salt may be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts may be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids," may include inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention may be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention may be presented as discrete units suitable for oral administration such as capsules, cachets or tablets each containing a predetermined amount of the active ingredient. Further, the compositions may be presented as a powder, as lyophilized powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, may also be administered by controlled release delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product may then be conveniently shaped into the desired presentation.

Thus, the pharmaceutical compositions of this invention may include a pharmaceutically acceptable carrier and either a compound of the invention described herein or a pharmaceutically acceptable salt of the compounds of the invention. The compounds of the invention, or pharmaceutically acceptable salts thereof, may also be included in pharmaceutical compositions in combination with one or more other therapeutically active compounds.

The pharmaceutical carrier employed may be, for example, a solid, liquid, or gas. Examples of solid carriers may include lactose, terra alba, sucrose, talc, gelatin, agar, pectin, acacia, magnesium stearate, and stearic acid. Examples of liquid carriers may include sugar syrup, peanut oil, olive oil, and water. Examples of gaseous carriers may include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Pharmaceutical compositions of the present invention suitable for parenteral administration may be prepared as solutions or suspensions of the active compounds in water. A suitable surfactant may be included such as, for example, hydroxypropylcellulose. Dispersions may also be prepared in glycerol, liquid polyethylene glycols, and mixtures thereof in oils. Further, a preservative may be included to prevent the detrimental growth of microorganisms.

Pharmaceutical compositions of the present invention suitable for injectable use include sterile aqueous solutions or dispersions. Furthermore, the compositions may be in the form of sterile powders for the extemporaneous preparation of such sterile injectable solutions or dispersions. In all cases, the final injectable form must be sterile and must be effectively fluid for easy syringe-ability. The pharmaceutical compositions must be stable under the conditions of manufacture and storage; thus, preferably should be preserved against the contaminating action of microorganisms such as bacteria and fungi. The carrier may be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention may be in a form suitable for topical use such as, for example, an aerosol, cream, ointment, lotion, dusting powder, mouth washes, gargles, and the like. Further, the compositions may be in a form suitable for use in transdermal devices. These formulations may be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention may be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants may be included to render the formulation isotonic with the blood of the intended recipient. Compositions containing a compound of the invention, and/or pharmaceutically acceptable salts thereof, may also be prepared in powder or liquid concentrate form.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

In one embodiment, an exemplary pharmaceutical composition may comprise an effective amount of the disclosed compounds (including pharmaceutically acceptable salt(s) thereof) as an active ingredient, a pharmaceutically acceptable carrier, and, optionally, other therapeutic ingredients or adjuvants. This pharmaceutical composition may comprise about 0.1% by weight to about 50% by weight of the disclosed compound, or more preferably about 10% by weight. This pharmaceutical composition may also comprise about 0.5% by weight to about 30% by weight of the disclosed compound, but more preferably about 5% by weight. A suitable treatment dose of this pharmaceutical composition, suitable for measured absorption (oral route; administered dose shall be based on actual uptake) or measured uptake (rectal route; administered dose based on actual uptake) or direct injection (intradermal or subcutaneous or intravenous), may be between 5 milligrams and 30 grams, or more preferably between 250 milligrams and 3 grams per dose.

Bimodal Use—Therapeutic and Diagnostic Methods

Diagnostic and therapeutic methods are disclosed for the in vivo modulation, eradication (i.e., lethality), and/or detection of diseases or conditions using the disclosed compounds. The overall construct of the dextran backbone with CD206 targeting moieties may be used for these purposes without added carrying moieties, chelation moieties, nor the chelation of cations where there is intent to therapeutically modulate macrophage states or expression. However, certain moieties may be added such that the modulation effect is retained while still providing for diagnostic purposes as well, making the overall schema bimodal.

In certain embodiments, the disclosed compounds include a detection label in addition to the therapeutic agent. As used herein, the term "detectable label or moiety" may refer to an atom, isotope, or chemical structure that is: (1) capable of attachment to the carrier molecule; (2) non-toxic to humans or other mammalian subjects; and (3) provides a directly or indirectly detectable signal, particularly a signal that is not only measurable, but whose intensity is related (e.g., proportional) to the concentration of the detectable moiety. The signal may be detected by any suitable method of detection, including spectroscopic, electrical, optical, magnetic, auditory, radio signal, or palpation detection.

Detection labels include, but are not limited to, fluorescent molecules (a.k.a. fluorochromes and fluorophores), chemiluminescent reagents (e.g., luminol), bioluminescent reagents (e.g., luciferin and green fluorescent protein (GFP)), metals (e.g., gold nanoparticles), and radioactive isotopes (radioisotopes). Suitable detection labels may be selected based on the choice of imaging method. For example, the detection label may be a near infrared fluorescent dye for optical imaging, a Gadolinium chelate for MRI imaging, a radionuclide for PET or SPECT imaging, or a gold nanoparticle for CT imaging.

Detection labels may be selected from, for example, a radionuclide, a radiological contrast agent, a paramagnetic ion, a metal, a fluorescent label, a chemiluminescent label, an ultrasound contrast agent, a photoactive agent, or a combination thereof. Non-limiting examples of detectable labels include a radionuclide such as $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn $^{55}$Co, $^{72}$As, $^{75}$Br, $^{76}$Br, $^{82m}$Rb, $^{83}$Sr, $^{117m}$Sn or other gamma-, beta-, or positron-emitters. Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III). Ultrasound contrast agents may comprise liposomes, such as gas-filled liposomes.

Other suitable labels include, for example, fluorescent labels (such as fluorescein, isothiocyanate, rhodamine, phycoerythrin, phycocyanin, allophycocyanin, o-phthaldehyde, and fluorescamine and fluorescent metals such as Eu or others metals from the lanthanide series), near IR dyes, quantum dots, phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes, metals, metals chelates or metallic cations or other metals or metallic cations that are particularly suited for use in in vivo, in vitro or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels include moieties that may be detected using NMR or ESR spectroscopy. Such labeled molecules may, for example, be used for in vitro, in vivo or in situ assays (including immunoassays known per se such as ELISA, RIA, EIA and other "sandwich assays," etc.) as well as in vivo diagnostic and imaging purposes, depending on the choice of the specific label. Another modification may involve the introduction of a chelating group, for example, to chelate one of the metals or metallic cations referred to above. Suitable chelating groups, for example, include, without limitation, diethyl-enetriaminepentaacetic acid (DTPA) or ethylenediaminetetraacetic acid (EDTA). Yet another modification may comprise the introduction of a functional group that is one part of a specific binding pair, such as the biotin-(strep) avidin binding pair. Such a functional group may be used to link a disclosed compound to a protein, polypeptide or chemical compound that is bound to the other half of the binding pair, i.e., through formation of the binding pair. For example, such a conjugated molecule may be used as a reporter, for example, in a diagnostic system where a detectable signal-producing agent is conjugated to avidin or streptavidin.

1. Optical Imaging

The disclosed compounds may include a detectable label useful for optical imaging. A number of approaches may be used for optical imaging. The various methods may depend upon fluorescence, bioluminescence, absorption or reflectance as the source of contrast. Fluorophores are compounds or moieties that absorb energy of a specific wavelength and re-emit energy at a different (but equally specific) wavelength. In certain embodiments, the detectable label is a near-infrared (NIR) fluorophore. Suitable NIRs include, but are not limited to, VivoTag-S® 680 and 750, Kodak X-SIGHT Dyes and Conjugates, DyLight 750 and 800 Fluors, Cy 5, Cy 5.5 and 7 Fluors, Alexa Fluor 680 and 750

Dyes, Alexa Fluor 688, and IRDye 680 and 800CW Fluors and combinations thereof. In certain embodiments, Quantum dots, with their photostability and bright emissions, may also be used with optical imaging.

2. Nuclear Medicine Imaging

The disclosed compounds may include a detectable label (e.g., a radionuclide) useful for nuclear medicine imaging. Nuclear medicine imaging involves the use and detection of radioisotopes in the body. Nuclear medicine imaging techniques include scintigraphy, single photon emission computed tomography (SPECT), and positron emission tomography (PET). In these techniques, radiation from the radioisotopes may be captured by a gamma camera to form two-dimensional images (scintigraphy) or 3-dimensional images (SPECT and PET).

Radioisotopes that may be incorporated into or attached directly to the disclosed compounds include, but are not limited to, tritium, $^{11}$C, $^{13}$N, $^{14}$C, $^{15}$O, $^{18}$H, $^{62}$Cu, $^{64}$Cu, $^{67}$Cu, $^{68}$Ga, $^{76}$Br, $^{82}$Rb, $^{90}$Y, $^{99m}$Tc, $^{111}$In, $^{123}$I, $^{124}$I, $^{125}$I, $^{131}$I, $^{153}$Sm, $^{201}$Tl, $^{186}$Re, $^{188}$Re, $^{117m}$Sn and $^{212}$Bi. In certain embodiments, the radioisotope is attached to a disclosed compound by halogenation. Radionuclides used in PET scanning are typically isotopes with short half-lives. Typical isotopes include $^{11}$C, $^{13}$N, $^{15}$O, $^{18}$F, $^{64}$Cu, $^{62}$Cu, $^{124}$I, $^{76}$Br, $^{82}$Rb and $^{68}$Ga, with $^{18}$F being the most clinically utilized.

Gamma radiation from radioisotopes may be detected using a gamma particle detection device. In some embodiments, the gamma particle detection device is a Gamma Finder® device (SenoRx, Irvine Calif.). In some embodiments, the gamma particle detection device is a Neoprobe® GDS gamma detection system (Cincinnati, Ohio).

Positron emission tomography is a nuclear medicine imaging technique which produces a three-dimensional image or picture of functional processes in the body. Some agents used for PET imaging provide information about tissue metabolism or some other specific molecular activity. Commonly used agents or potential agents that may be used as detectable agents include, but are not limited to: $^{64}$Cu diacetyl-bis(N$^4$-methylthiosemicarbazone); $^{18}$F-fluorodeoxyglucose (FDG); $^{18}$F-fluoride; 3'-deoxy-3'-[$^{18}$F]fluorothymidine (FLT); $^{18}$F-fluoromisonidazole; Gallium; Technetium-99m; and Thallium. Radiopaque diagnostic agents may be selected from compounds, barium compounds, gallium compounds, and thallium compounds. A wide variety of fluorescent labels are known in the art, including, but not limited to, fluorescein isothiocyanate, rhodamine, phycoerythrin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

A number of trivalent metal radionuclides have physical properties suitable for radioisotope imaging (e.g., indium-111 ($^{111}$In) gallium-67/68 ($^{67/68}$Ga) and yttrium-86 ($^{86}$Y)) or for targeted radionuclide therapy (e.g., $^{90}$Y and lutetium-177 ($^{177}$Lu)). Diethylenetriaminepentaacetic acid (DTPA) and/or 1,4,7,10-tetraazacyclododecane-1,4,7,10-tetraacetic acid (DOTA; CAS 60239-18-1) may be used (see Choe and Lee, 2007, Current Pharmaceutical Design, 13:17-31; Li et al., 2007, J. Nuclear Medicine, "$^{64}$Cu-Labeled Tetrameric and Octameric RGD Peptides for Small-Animal PET of Tumor avb3 Integrin Expression", 48:1162-1171; Nahrendorf et al, 2009, JACC Cardiovasc. Imaging, 2:10:1213-1222; Li et al., 2009, Mol. Cancer Ther., 8:5:1239-1249; Yim et al., 2010, J. Med. Chem., 53:3944-3953; Dijkgraaf et al., 2010, Eur. J. Nucl. Med. Mol. Imaging, published online 21 Sep. 2010; U.S. patent application Ser. No. 10/792,582; Dransfield et al., U.S. Pat. Pub. Nos. US 2010/0261875; U.S. Pat. No. 7,666,979). Of the metals mentioned, the DOTA complexes are more thermodynamically and kinetically stable than the DTPA complexes (see Sosabowski et al., Nature Protocols 1, -972-976 (2006) and Leon-Rodriguez et al., Bioconjugate chemistry, Jan. 3, 2008; 19(2):391-402).

3. Magnetic Resonance Imaging

The disclosed compounds may be detected via magnetic resonance imaging. MRI has the advantages of having very high spatial resolution and is very adept at morphological imaging and functional imaging. MRI generally has a sensitivity of around 1 milli-mol/L to 10 micro-mol/L. Improvements to increase MR sensitivity include hyperpolarization by increasing magnetic field strength, optical pumping, or dynamic nuclear polarization. There are also a variety of signal amplification schemes based on chemical exchange that increase sensitivity.

4. Chelating Agents

In some embodiments, a chelating agent may be attached or incorporated into a disclosed compound, and used to chelate a therapeutic or diagnostic agent, such as a radionuclide. Exemplary chelators include, but are not limited to, DTPA (such as Mx-DTPA), DOTA, TETA, NETA or NOTA. Other useful chelators include, but are not limited to, DTPA, DO3A, DOTA, EDTA, TETA, EHPG, HBED, NOTA, DOTMA, TETMA, PDTA, TTHA, LICAM, HYNIC, and MECAM. HYNIC is particularly useful for chelating technetium-99 (Tc99), another imaging agent of the invention.

5. Actions Based on Imaging and Identifications

The disclosed methods include the determination, identification, indication, correlation, diagnosis, prognosis, etc. (which may be referred to collectively as "identifications") of subjects, diseases, conditions, states, etc. based on imaging, measurements, detections, comparisons, analyses, assays, screenings, etc. For example, the disclosed imaging methods may enable the identification of patients, organs, tissues, etc. having cancer cells, metastasized cancer cells, cancer cells beyond tumor margins, etc. With this knowledge, it may be possible to determine specific actions (e.g., treatment, behaviors, etc.) that may be taken to address the cancer (i.e., cancer cells, metastasized cancer cells, cancer cells beyond tumor margins) that may be suitable for the identified patients, organs, tissues, etc., but not for others (e.g., subjects not diagnosed with a particular disease or condition). This ability to differentiate between who would benefit from the specific actions, and who would not, may thereby facilitate the efficient administration of treatment by ensuring that only those who need or would otherwise benefit from it will receive it, and those who do not need or would otherwise benefit from it will not receive it. Of course, this is just one non-limiting example as such identifications are useful for many other reasons.

Accordingly, also disclosed herein are methods that comprise taking particular actions following and based on the disclosed identifications. For example, disclosed are methods that comprise creating a record of an identification in a physical (e.g., paper), electronic, or other form. Thus, creating a record of an identification based on the disclosed methods differs physically and tangibly from merely performing an imaging, measurement, detection, comparison, analysis, assay, screen, etc. Such a record is particularly substantial and significant in that it allows the identification to be fixed in a tangible form that may be, for example, communicated to others (such as those who could treat, monitor, follow-up, advise, etc. the subject based on the identification); retained for later use or review; used as data to assess sets of subjects, treatment efficacy, accuracy of identifications based on different imaging, measurements, detections, comparisons, analyses, assays, screenings, etc., and the like. Such uses of records of identifications may be made, for example, by the same individual or entity as, by a different individual or entity than, or a combination of the same individual or entity as and a different individual or entity than, the individual or entity that made the record of the identification. The disclosed methods of creating a record may be combined with any one or more other methods disclosed herein, and in particular, with any one or more steps of the disclosed methods of identification.

As another example, disclosed are methods that comprise making one or more further identifications based on one or more other identifications. For example, particular treatments, monitoring, follow-up, advice, etc. may be identified based on the other identification. For example, identification of a subject that has a disease or condition with a high level of a particular component or characteristic may be further identified as a subject that could or should be treated with a therapy based on or directed to the high-level component or characteristic. A record of such further identifications may be created (as described above, for example) and may be used in any suitable way. Such further identifications may be based, for example, directly on the other identifications, a record of such other identifications, or a combination thereof. Such further identifications may be made, for example, by the same individual or entity as, by a different individual or entity than, or a combination of the same individual or entity as and a different individual or entity than, the individual or entity that made the other identifications. The disclosed methods of making a further identification may be combined with any one or other methods disclosed herein, and in particular, with any one or more steps of the disclosed methods of identification.

As another example, disclosed are methods that comprise treating, monitoring, following-up with, advising, etc. a subject identified in any of the disclosed methods. Also disclosed are methods that comprise treating, monitoring, following-up with, advising, etc. a subject for which a record of an identification from any of the disclosed methods has been made. For example, particular treatments, monitoring, follow-up, advice, etc. may be used based on an identification and/or based on a record of an identification. For example, a subject identified as having a disease or condition with a high-level of a particular component or characteristic (and/or a subject for which a record has been made of such an identification) may be treated with a therapy based on or directed to the high-level component or characteristic. Such treatments, monitoring, follow-ups, advice, etc. may be based, for example, directly on identifications, a record of such identifications, or a combination thereof. Such treatments, monitoring, follow-ups, advice, etc. may be performed, for example, by the same individual or entity as, by a different individual or entity than, or a combination of the same individual or entity as and a different individual or entity than, the individual or entity that made the identifications and/or record of the identifications. The disclosed methods of treating, monitoring, following-up with, advising, etc. may be combined with any one or more other methods disclosed herein, and in particular, with any one or more steps of the disclosed methods of identification.

6. Methods of Treatment

Methods of treating or preventing diseases or disorders are provided using the disclosed compounds. The disclosed compounds may be used for targeting CD206 high expressing cells and/or macrophages for the treatment of intracellular pathogens. Some embodiments as disclosed herein may include targeting cells that do not express CD206. The disclosed compounds may further be used to target tumor-associated macrophages, e.g. to be used for treating cancer.

Macrophage-related and other CD206 high expressing cell-related diseases for which the compositions and methods herein may be used include, but are not limited to: Covid-19 (SARS-Cov-2, and corona viruses and other RNA or DNA viruses), parasites, acquired immune deficiency syndrome (AIDS), acute disseminated encephalomyelitis (ADEM), Addison's disease, agammaglobulinemia, allergic diseases, alopecia areata, Alzheimer's disease, amyotrophic lateral sclerosis, ankylosing spondylitis, antiphospholipid syndrome, antisynthetase syndrome, arterial plaque disorder, asthma, atherosclerosis, atopic allergy, atopic dermatitis, autoimmune aplastic anemia, autoimmune cardiomyopathy, autoimmune enteropathy, autoimmune hemolytic anemia, autoimmune hepatitis, autoimmune hypothyroidism, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticarial, autoimmune uveitis, Balo disease/Balo concentric sclerosis, Behçet's disease, Berger's disease, Bickerstaff's encephalitis, Blau syndrome, bullous pemphigoid, Castleman's disease, celiac disease, Chagas disease, chronic inflammatory demyelinating polyneuropathy, chronic recurrent multifocal osteomyelitis, chronic obstructive pulmonary disease, chronic venous stasis ulcers, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's Syndrome, cutaneous leukocytoclastic angiitis, Dego's disease, Dercum's disease, dermatitis herpetiformis, dermatomyositis, Diabetes mellitus type I, Diabetes mellitus type II diffuse cutaneous systemic sclerosis, Dressler's syndrome, drug-induced lupus, discoid lupus erythematosus, eczema, emphysema, endometriosis, enthesitis-related arthritis, eosinophilic fasciitis, eosinophilic gastroenteritis, eosinophilic pneumonia, epidermolysis bullosa acquisita, erythema nodosum, erythroblastosis fetalis, essential mixed cryoglobulinemia, Evan's syndrome, fibrodysplasia ossificans progressive, fibrosing alveolitis (or idiopathic pulmonary fibrosis), gastritis, gastrointestinal pemphigoid, Gaucher's disease, glomerulonephritis, Goodpasture's syndrome, Graves' disease, Guillain-Barré syndrome (GBS), Hashimoto's encephalopathy, Hashimoto's thyroiditis, heart disease, Henoch-Schonlein purpura, herpes gestationis (aka gestational pemphigoid), hidradenitis suppurativa, HIV infection, Hughes-Stovin syndrome, hypogammaglobulinemia, infectious diseases (including bacterial infectious diseases), idiopathic inflammatory demyelinating diseases, idiopathic pulmonary fibrosis, idiopathic thrombocytopenic purpura, IgA nephropathy, inclusion body myositis, inflammatory arthritis, inflammatory bowel disease, inflammatory dementia, interstitial cystitis, interstitial pneumonitis, juvenile idiopathic arthritis (aka juvenile rheumatoid arthritis), Kawasaki's disease, Lambert-Eaton myasthenic syndrome, leukocytoclastic vasculitis, lichen planus, lichen sclerosus, linear IgA disease (LAD), lupoid hepatitis (aka autoimmune hepatitis), lupus erythematosus, lymphomatoid granulomatosis, Majeed syndrome, malignancies including cancers (e.g., sarcoma, Kaposi's sarcoma, lymphoma, leukemia, carcinoma and melanoma), Meniere's disease, microscopic polyangiitis, Miller-Fisher syndrome, mixed connective tissue disease, morphea, Mucha-Habermann disease (aka *Pityriasis lichenoides et varioliformis acuta*), multiple sclerosis, myasthenia gravis, myositis, narcolepsy, neuromyelitis optica (aka Devic's disease), neuromyotonia, occular cicatricial pemphigoid, opsoclonus myoclonus syndrome, Ord's thyroiditis, palindromic rheumatism, PANDAS (pediatric autoimmune neuropsychiatric disorders associated with *streptococcus*), paraneoplastic cerebellar degeneration, Parkinsonian disorders, paroxysmal nocturnal hemoglobinuria (PNH), Parry Romberg syndrome, Parsonage-Turner syndrome, pars planitis, pemphigus vulgaris, peripheral artery disease, pernicious anaemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restenosis, restless leg syndrome, retroperitoneal fibrosis, rheumatoid arthritis, rheumatic fever, sarcoidosis, schizophrenia, Schmidt syndrome, Schnitzler syndrome, scleritis, scleroderma, sepsis, serum Sickness, Sjögren's syndrome, spondyloarthropathy, Still's disease (adult onset), stiff person syndrome, stroke, subacute bacterial endocarditis (SBE), Susac's syndrome, Sweet's syndrome, Sydenham chorea, sympathetic ophthalmia, systemic lupus erythematosus, Takayasu's arteritis, temporal arteritis (aka "giant cell arteritis"), thrombocytopenia, Tolosa-Hunt syndrome,) transplant (e.g., heart/lung transplants) rejection reactions, transverse myelitis, tuberculosis, ulcerative colitis, undifferentiated connective tissue disease, undifferentiated spondyloarthropathy, urticarial vasculitis, vasculitis, vitiligo, and Wegener's granulomatosis.

Mannose receptor protein CD206 is a C-type lectin binding protein found on the surface of macrophages and certain other cells (e.g., Kaposi's sarcoma spindle cells). Tilmanocept, related carrier molecules described in the '990 Patent, and other dextran backbone-based carrier molecules, may bind exclusively to CD206 when administered to mammals or when contacted with CD206 high expressing cells ex vivo. No other receptors are believed to bind or transduce these carrier molecules, even though there are numerous other mannose receptors found in mammals. This finding—that CD206 is the sole gateway for tilmanocept binding in mammalian patients—may enable MAD carrier molecules (and related carrier molecules) to be used as the basis for preparing a variety of therapeutically and diagnostically effective molecular species for use in the diagnosis and/or treatment of macrophage related diseases and other diseases mediated by CD206 high expressing cells.

The disclosed compounds may include therapeutic agents including, but not limited to, cytotoxic agents, anti-angiogenic agents, pro-apoptotic agents, antibiotics, hormones, hormone antagonists, chemokines, drugs, prodrugs, toxins, enzymes, or other agents. The disclosed compounds may also include chemotherapeutic agents; antibiotics; immunological adjuvants; compounds useful for treating tuberculosis; steroids; nucleotides; peptides; or proteins.

In certain embodiments, the compounds include an antimicrobial drug selected from the group comprising or consisting of: an antibiotic; an anti-tuberculosis antibiotic (such as isoniazid, ethambutol); an anti-retroviral drug, for example an inhibitor of reverse transcription (such as zidovudin) or a protease inhibitor (such as indinavir); drugs with effect on leishmaniasis (such as Meglumine antimoniate), or any combination thereof. In certain embodiments, the compounds include an anti-microbial active, such as amoxicillin, ampicillin, tetracyclines, aminoglycosides (e.g., streptomycin), macrolides (e.g., erythromycin and its relatives), chloramphenicol, ivermectin, rifamycins and polypeptide antibiotics (e.g., polymyxin, bacitracin) and zwittermicin. In certain embodiments, the compounds include an active selected from isoniazid, doxorubicin, streptomycin, and tetracycline, or any combination thereof. The disclosed compounds may be used, for example, to treat Tuberculosis, Covid-19 (SARS-covid-2 and other RNA or DNA viruses), *Staphylococcus, Streptococcus*, yeast, *Serratia. E. coli*, and *Pseudomonas aeruginosa*.

In certain embodiments, the disclosed compounds advantageously have efficacy in the treatment of a condition, disease, or disorder caused by cellular or acellular microorganisms such as, for example, Corona viruses.

In certain embodiments, the disclosed compounds include a chemotherapeutic agent for the treatment or prevention of cancer. The cancer may be any cancer cell capable of metastasis. For example, the cancer may be a sarcoma, lymphoma, leukemia, carcinoma, blastoma, or germ cell tumor. A representative but non-limiting list of cancers that the disclosed compositions may be used to treat or prevent include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers, testicular cancer; colon and rectal cancers, prostatic cancer, and pancreatic cancer.

In certain embodiments, the disclosed compounds are effective for treating autoimmune diseases, such as rheumatoid arthritis, lupus (SLE), or vasculitis. In certain embodiments, the disclosed compounds are effective for treating an inflammatory disease, such as Crohn's disease, inflammatory bowel disease, or collagen-vascular diseases.

In certain embodiments, the disclosed compounds are effective for targeting, treating, and inflammatory-state shifting macrophages and their phenotype in such a way that is beneficial to the condition of a patient.

One of ordinary skill in the art will appreciate that various kinds of molecules and compounds (e.g., therapeutic agents, detection labels, and combinations thereof) may be delivered to a cell or tissue using the disclosed compounds.

7. Administration

The disclosed compounds may be administered via any suitable method. For example, the disclosed compounds may be administered parenterally into the parenchyma of targeted organs or structures (e.g., tumors), or administered such that the disclosed compounds enter the bloodstream and circulates to the targeted tissue. In one or more embodiments, the disclosed compounds may be administered directly into or adjacent to a tumor mass. Other methods of administration may include administering the disclosed compound intravenously, intraperitoneally, intramuscularly, subcutaneously, intracavity, and/or transdermally.

Parenteral administration of the compounds, if used, is generally characterized by injection. Injectables may be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

EXAMPLES

Example 1: Cy3-Tilmanocept Binding to Human Macrophages

FIG. 1 lead-in cartoon indicates the structure of tilmanocept with the dextran backbone in green, the CD206 mannose binding moieties in blue, and the DTPA chelating group in red (which may be replaced by a fluorescent chemical entity as noted in FIG. 1 (B-frame). The blue-boxed cartoon structure indicates the structural elements of CD206, the target for the tilmanocept. This receptor contains three mannose specific binding sites (noted as orange "V'"s, binding the mannose moieties of the tilmanocept molecule). The $K_d$ for tilmanocept/CD206 is ~$3\times10^{-11}$ M.

A quantity of macrophages was cultured for 5 days to enable blood monocytes to differentiate into macrophages (human monocyte-derived macrophages, or "MDMs"), and then pre-treated with or without siRNA (siRNA is employed to block the production of CD206, the receptor for tilmanocept). FIG. 1(A-frame) shows the Western blot of the protein from macrophages indicating the loss of protein expression of CD206 and no reduction on beta-actin (a control protein that is unaffected by siRNA specifically for CD206). FIG. 1 (B-frame) indicates that the red fluorescence, which represents tilmanocept binding to CD206 in living macrophages, is lost after siRNA inhibition of CD206 protein expression in the living macrophages. Lastly, FIG. 1 (C-frame quantitatively measures the amount of red fluorescence from FIG. 1 (B-frame), realizing a nearly complete loss of the CD206 presence as measured by fluorescence tilmanocept binding. (**P <0.005).

Example 2: Covid-19 (SARS-Covid-2) Virus

Tilmanocept and its equivalents are discussed in WO 2016/118188 published Jul. 28, 2016 from application PCT/US2015/041036, the entirety of which is incorporated herein by reference.

Viruses, including Covid-19 (Severe acute respiratory syndrome coronavirus 2, SARS-covid-2 and/or COVID-19) (exemplification referred to as Wuhan virus, Chinese corona virus, Covid-19) can cause Covid-19 virus disease (or, at times, referred to as SARS) and is the strain of coronavirus that causes coronavirus disease 2019 (COVID-19), a respiratory illness. Colloquially known as coronavirus, it was previously referred to by its provisional name 2019 novel coronavirus (2019-nCoV). As described by the National Institutes of Health, it is the successor to SARS-CoV-1. SARS-CoV-2 is a positive-sense single-stranded RNA virus. It is contagious in humans, and the World Health Organization (WHO) has designated the ongoing pandemic of COVID-19 (temporally, December, 2019 thru months of 2020, and beyond) a Public Health Emergency of International Concern. Taxonomically, SARS-CoV-2 is a strain of severe acute respiratory syndrome-related coronavirus (SARSr-CoV). It is believed to have zoonotic origins and has close genetic similarity to bat coronaviruses, suggesting it emerged from a bat-borne virus. The virus shows little genetic diversity, indicating that the spillover event introducing SARS-CoV-2 to humans is likely to have occurred in late 2019. Epidemiological studies estimate each infection results in 1.4 to 3.9 new ones when no members of the community are immune and no preventive measures taken. The virus primarily spreads between people through close contact and via respiratory droplets produced from coughs or sneezes. It mainly enters human cells by binding to the receptor angiotensin converting enzyme 2 (ACE2) of the upper respiratory tract and nares.

While the Covid-19 virus has been shown to expressly enter and infect cells and human subjects via the ACE2 receptor (angiotensin converting enzyme-2, ACE-2), these disclosures provide an unexpected finding that macrophages in the lungs and liver are solely the harbingers of the Covid-19 virus and that this relationship appears to be the driving element of the disposition of the pulmonary disease as well as the disseminated involvement of other organs leading to the thrombosis cascade or other clotting within the alveoli and vessels of the lungs and other larger bodily blood vessels. FIG. 2 through FIG. 13 depict the results from the immunohistochemistry probing of several cadaveric tissue samples that were derived from deceased persons confirmed to have expired from Covid-19 disease. These stained cells images reveal that Covid-infected macrophages express CD206, the specific receptor for the agent(s) outlined in this application.

Figure 2:
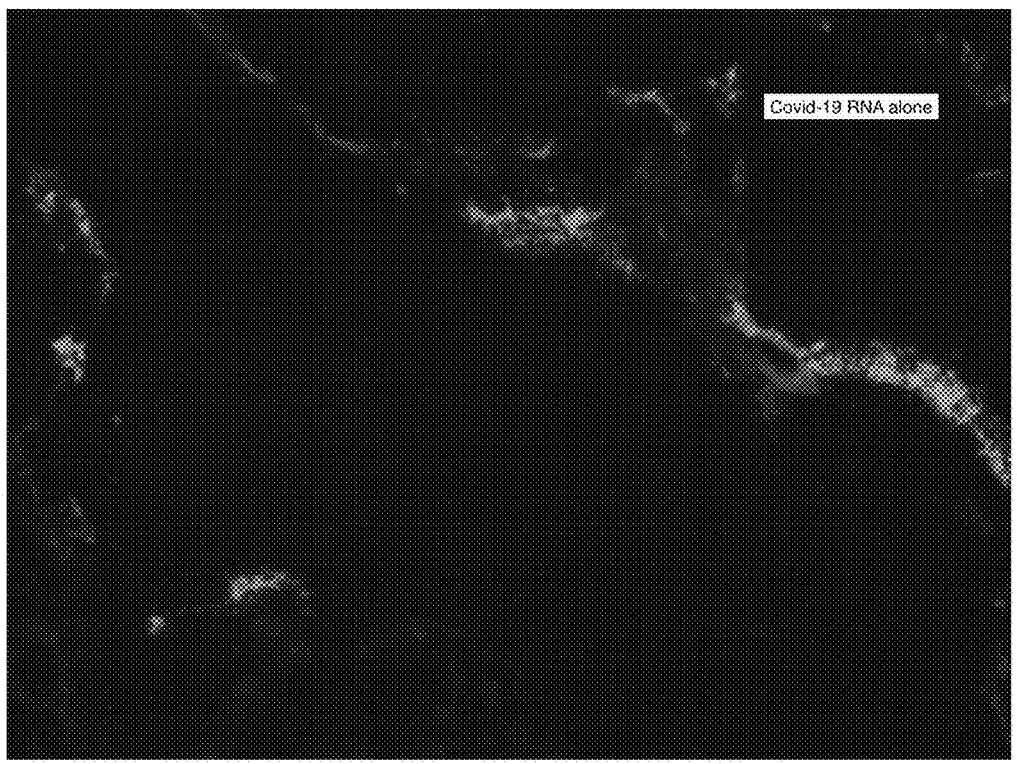

FIG. 2 is a stained fluorescence cell imaging of lung alveolar structures of a patient deceased by COVID-19. The cells were stained using a blue-fluorescent DNA stain (e.g., 4',6-diamidino-2-phenylindole, also known as DAPI, available from Thermo Fisher Scientific, Inc. of Waltham, Mass.) and a proprietary antisense SARS-2-Covid (Covid-19) probe containing indocyanine green. The cells were then imaged using an A1 HD25/A1R HD25 confocal microscope with dye-specific filter assessment. Cell nuclei and diffuse cell bodies are shown in blue (DAPI) while SARS-2-Covid RNA (Covid-19 Virus) is shown in green. As those skilled in the art will appreciate, the specificity of these fluorescence reporting colors is extremely high for the cell morphology and the localization of the virus.

Figure 3:
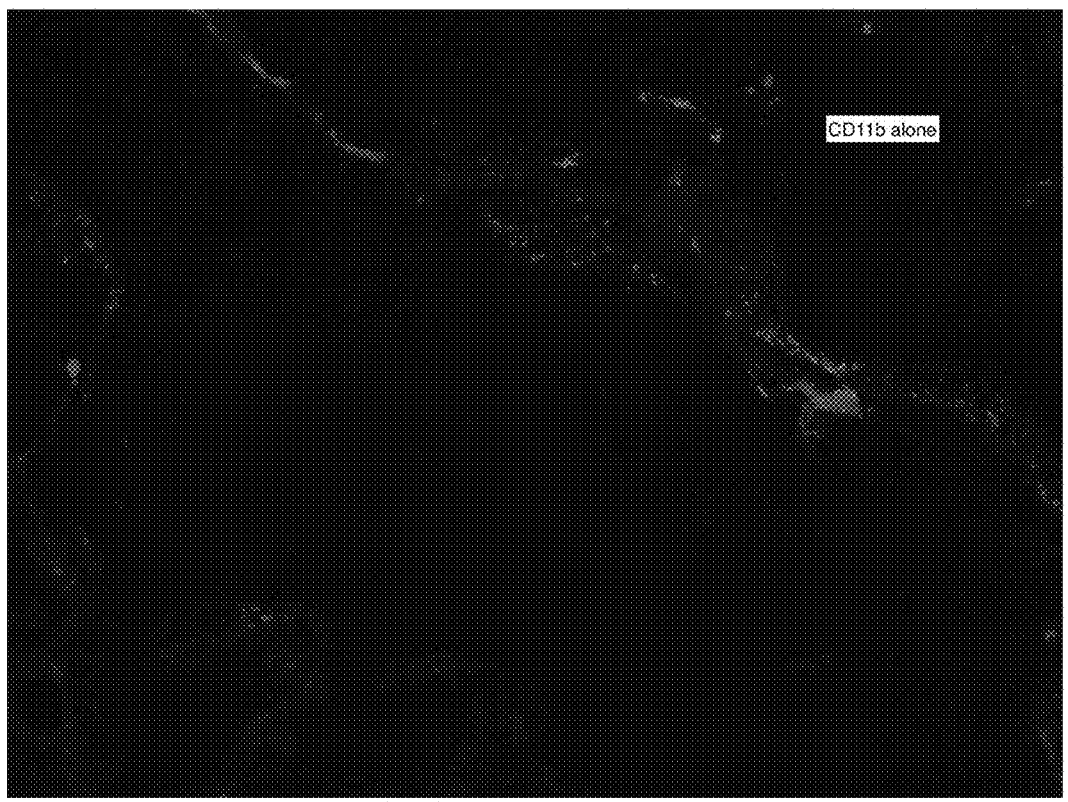

FIG. 3 is a stained cell image of lung alveolar structures of a patient deceased by COVID-19. The cells were imaged with nuclear localizing stains linked to fluorescence reporters. More specifically, the cells were stained using a blue-fluorescent DNA stain (e.g., DAPI) and a myeloid cell-identifying monoclonal antibody for CD11b containing a red fluorophore (e.g., Invitrogen Alexa Fluor 594 available from Thermo Fisher Scientific, Inc. of Waltham, Mass.). The cells were then imaged using an A1 HD25/A1R HD25 confocal microscope with dye-specific filter assessment. Cell nuclei and diffuse cell bodies are shown in blue (DAPI) while the myeloid/macrophage-targeting Alexa-monoclonal antibody (anti-CD11b) is shown in red. As those skilled in the art will appreciate, the specificity of these reporting colors is extremely high for the cell morphology and the localization of the CD11b marker glycoprotein.

Figure 4:
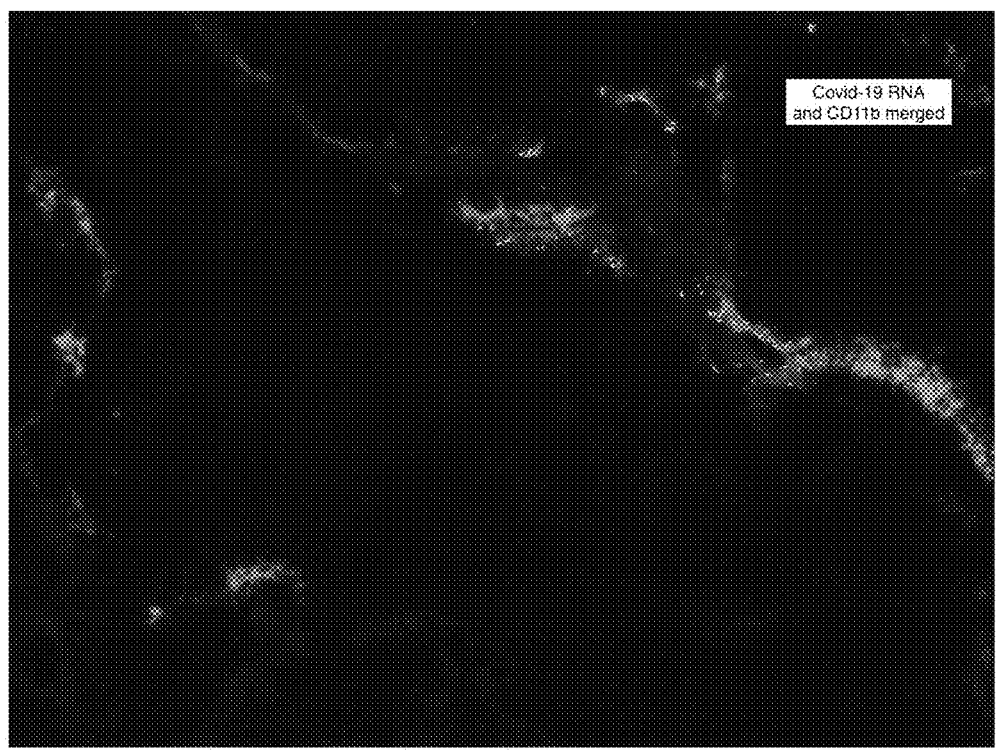

FIG. 4 is a merging of the images in FIGS. 2 and 3 to demonstrate the colocalization of the macrophage cell marker (CD11b) and the SARS-2-Covid (Covid-19) virus (yellow when colocalized). As those skilled in the art will appreciate, the tissue slices are the same as in FIGS. 2 and 3, and the merging of these images is significant evidence of the localization of the infectious agent (SARS-2-covid) with the macrophage cells.

Figure 5:
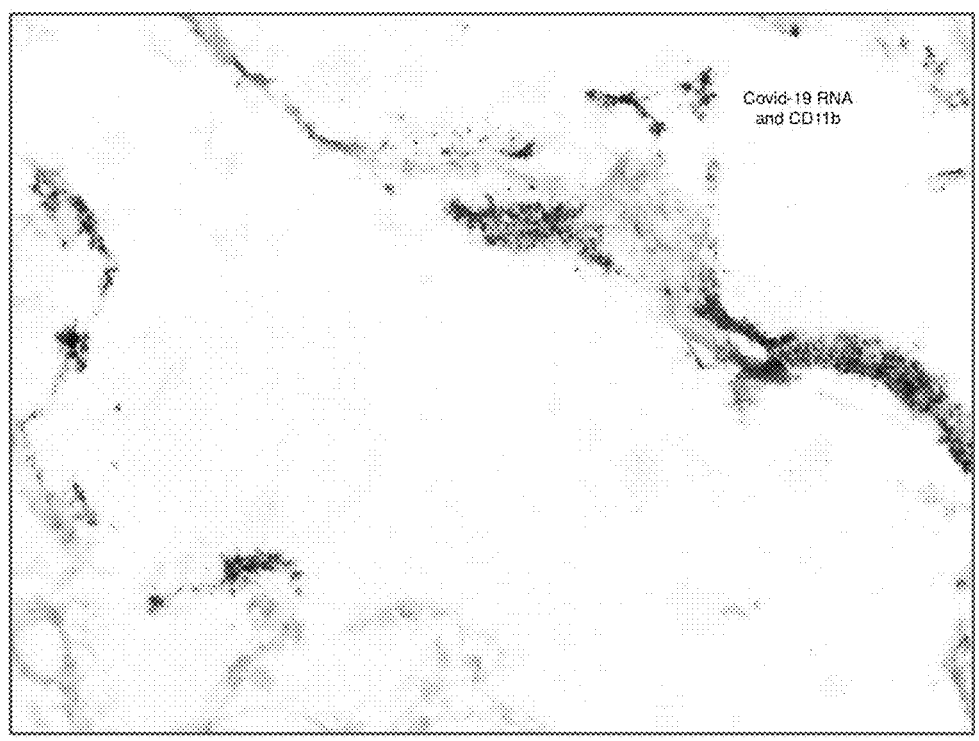

FIG. 5 is a stained cells image of lung alveolar structures of a patient deceased by COVID-19 that was taken using light microscopy imaging. This image employs the same tissue sections as in FIGS. 2-4, but utilizes an alternative colorization that reports under visible light using an A1 HD25/A1R HD25 confocal microscope. The cells were stained using visible blue dye (e.g., DAPI), Anti-CD11b containing red fluorophore (e.g., Invitrogen Alexa Fluor 594), and peroxidase/anti-peroxidase staining (with anti-sense RNA to the SARS-2-Covid (Covid-19) virus). Cell nuclei and diffuse cell bodies are shown in blue (DAPI), the myeloid/macrophage-targeting Alexa-monoclonal antibody (anti-CD11b) is shown in red, and Covid-19 is shown in brown. The merging of these markers (red stippling for CD11b and brown for Covid-19) is significant evidence of the localization of the infectious agent (SARS-2-Covid) with the macrophage cells.

Figure 6:
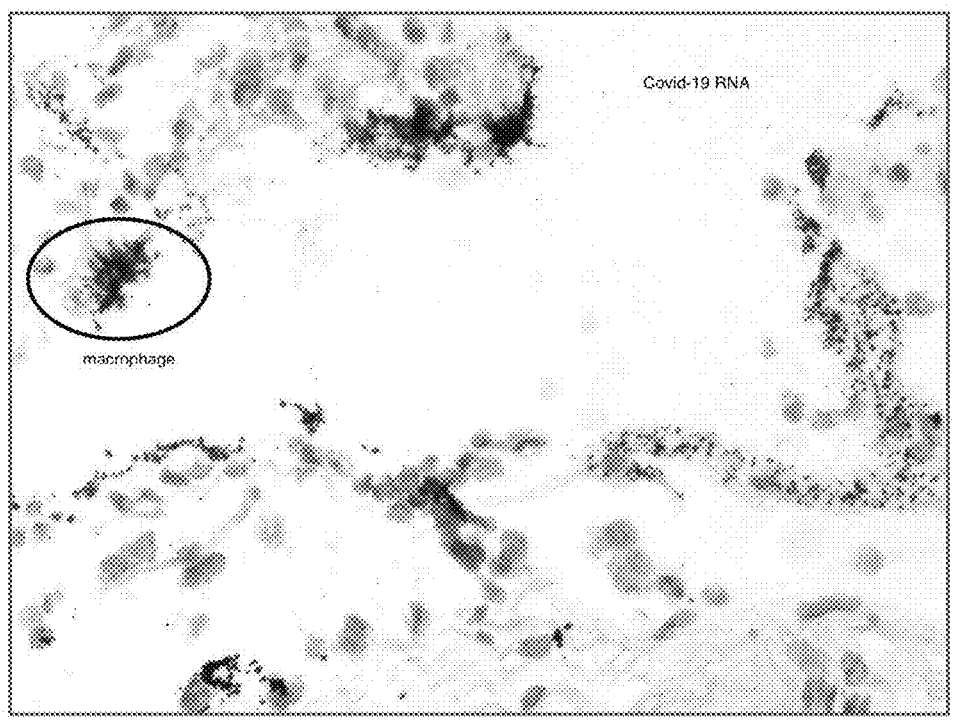

FIG. 6 is a stained cells image of lung alveolar structures of a patient deceased by COVID-19 that was taken using light microscopy imaging. This image employs different tissue sections than the tissue sections used in FIGS. 2-5, and utilizes an alternative colorization that reports under visible light using an A1 HD25/A1R HD25 confocal microscope. The cells were stained using a visible blue dye (e.g., hematoxylin), Anti-CD11b containing red fluorophore (e.g., Invitrogen Alexa Fluor 694), and peroxidase/anti-peroxidase staining (with antisense RNA to the SARS-2-Covid (Covid-19) virus). Cell nuclei and diffuse cell bodies are shown in blue, the myeloid/macrophage-targeting Alexa-monoclonal antibody (anti-CD11b) is shown in red, and Covid-19 is shown in brown. The merging of these markers (red stippling for CD11b and brown for Covid-19) is significant evidence of the localization of the infectious agent (SARS-2-Covid) with the macrophage cells.

Figure 7:
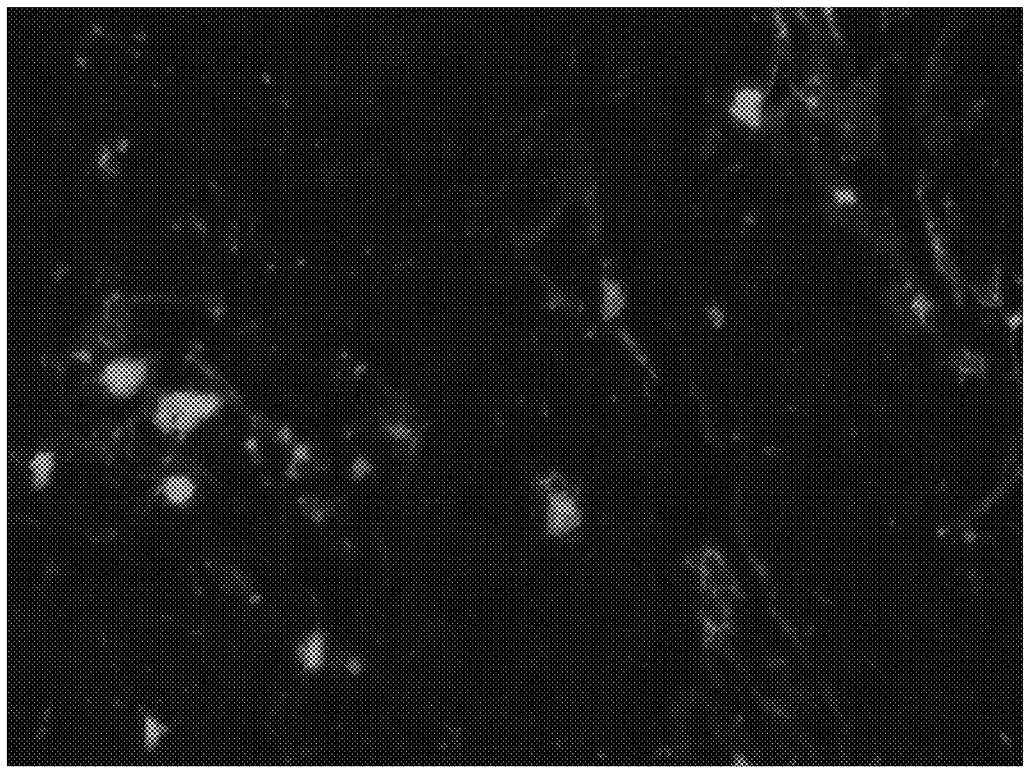

FIG. 7 is a stained fluorescence cell imaging of lung alveolar structures of another patient deceased by COVID-19. The cells were stained using a blue-fluorescent DNA stain (e.g., DAPI) and an antisense SARS-2-Covid (Covid-19) antisense probe containing indocyanine green. The cells were then imaged using an A1 HD25/A1R HD25 confocal microscope with dye-specific filter assessment. Cell nuclei and diffuse cell bodies are shown in blue (DAPI) while SARS-2-Covid RNA (Covid-19 Virus) is shown in green. As those skilled in the art will appreciate, the specificity of these fluorescence reporting colors is extremely high for the cell morphology and the localization of the virus.

Figure 8:
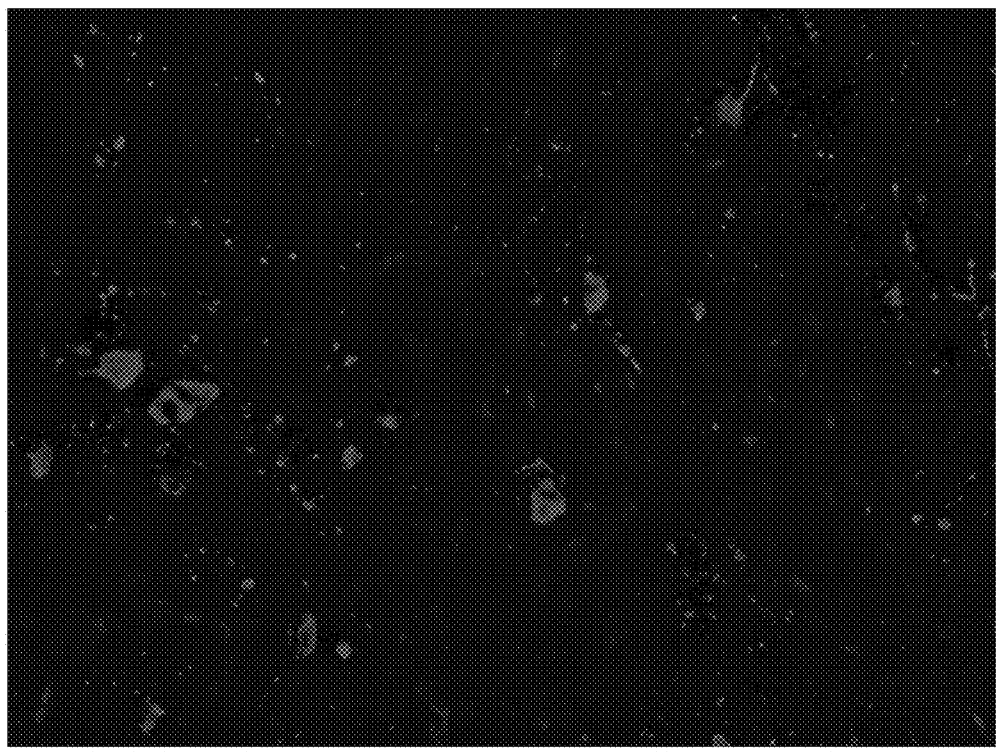

FIG. 8 is a stained cell image of lung alveolar structures of a patient deceased by COVID-19. The cells were imaged with nuclear localizing stains linked to fluorescence reporters. More specifically, the cells were stained using a blue-fluorescent DNA stain (e.g., DAPI) and a macrophage cell-identifying monoclonal antibody for CD206 (e.g., antiCD206 which is a glycoprotein with lectin-binding domain) that contains a red fluorophore (e.g., Invitrogen Alexa Fluor 594). The cells were then imaged using an A1 HD25/A1R HD25 confocal microscope with dye-specific filter assessment. Cell nuclei and diffuse cell bodies are shown in blue (DAPI) while the macrophage-targeting Alexa-monoclonal antibody (anti-CD206) is shown in red. As those skilled in the art will appreciate, the specificity of these reporting colors is extremely high for the cell morphology and the localization of the CD206 marker glycoprotein.

Figure 9:
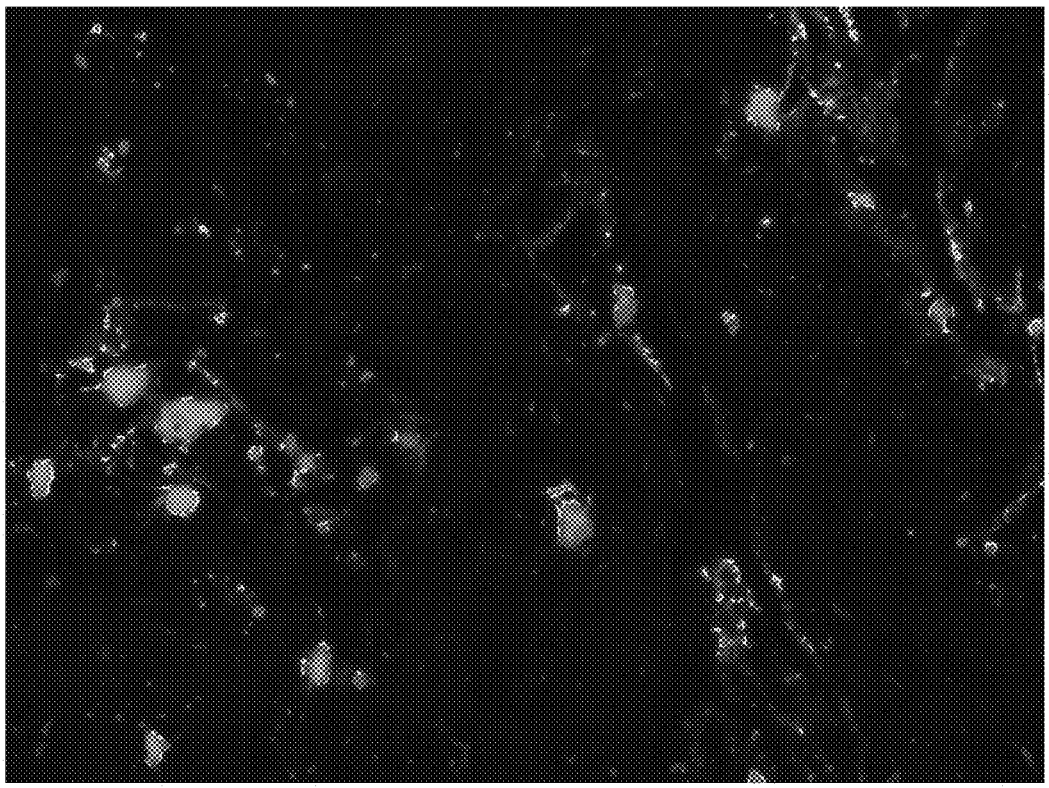

FIG. 9 is a merging of the images in FIGS. 7 and 8 to demonstrate the co-localization of the macrophage cell marker (CD206) and the SARS-2-Covid (Covid-19) virus (yellow when markers are colocalized). As those skilled in the art will appreciate, the tissue slices are exactly the same (FIGS. 7 and 8) and the merging of these markers is significant evidence of the specific localization of the infectious agent (SARS-2-covid) with the macrophage cells.

Figure 10:
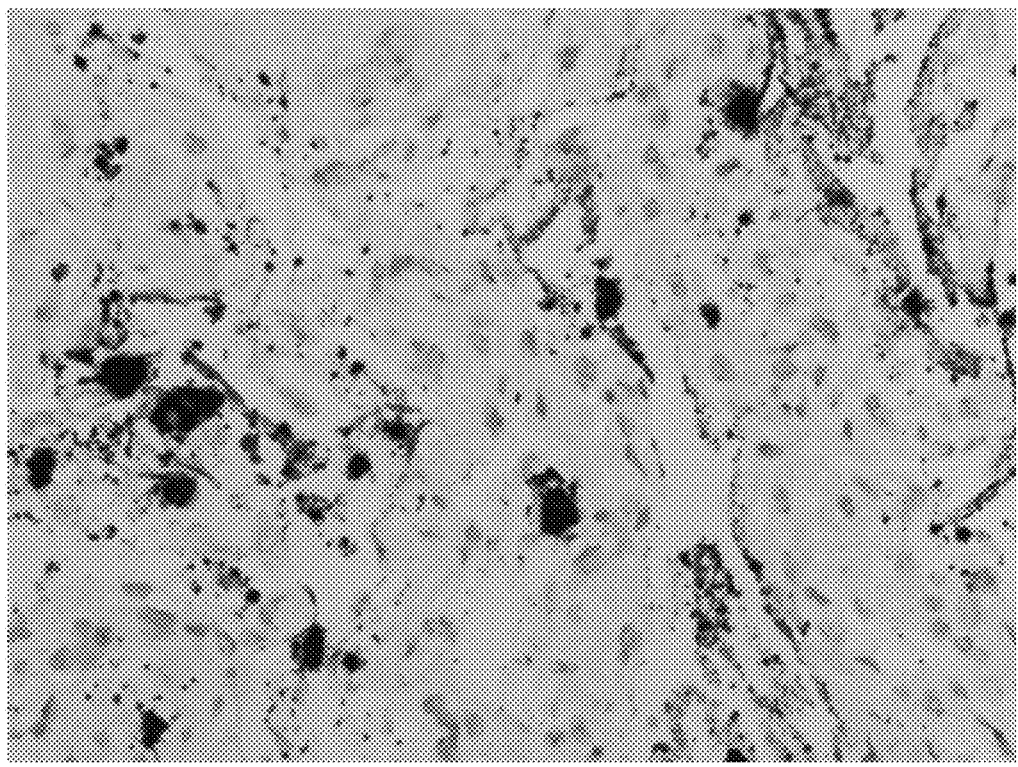

FIG. 10 is a stained cells image of lung alveolar structures of a patient deceased by COVID-19 that was taken using light microscopy imaging. This image employs different, but similar, tissue sections than the tissue sections used in FIGS. 7-9, and utilizes an alternative colorization that reports under visible light using an A1 HD25/A1R HD25 confocal microscope. The cells were stained using visible blue dye (e.g., hematoxylin), Anti-CD206 containing red fluorophore (e.g., Invitrogen Alexa Fluor 594), and peroxidase/anti-peroxidase staining (with antisense RNA to the SARS-2-Covid (Covid-19) virus). Cell nuclei and diffuse cell bodies are shown in blue, the myeloid/macrophage-targeting Alexa-monoclonal antibody (anti-CD206) is shown in red, and Covid-19 is shown in brown. The merging of these markers (red stippling for CD206 and brown for Covid-19) is significant evidence of the localization of the infectious agent (SARS-2-Covid) with the macrophage cells.

Figure 11:
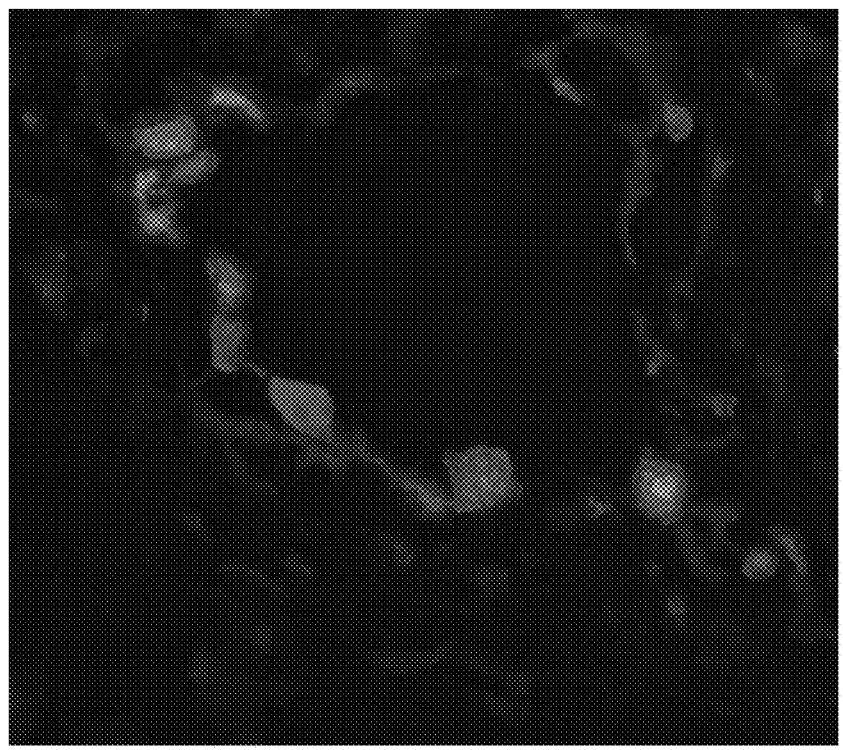

FIG. 11 is a stained fluorescence cell imaging of lung alveolar structures of another patient deceased by COVID-19. The cells were stained using a blue-fluorescent DNA stain (e.g., DAPI) and a Covid-19 anti-nucleocapsid protein antibody (Covid-19) containing indocyanine green. The cells were then imaged using an A1 HD25/A1R HD25 confocal microscope with dye-specific filter assessment. Cell nuclei and diffuse cell bodies are shown in blue (DAPI) while SARS-2-Covid RNA capsid protein is shown in green. As those skilled in the art will appreciate, the specificity of localization of the viral nucleocapsid protein in the cells based on the fluorescence reporting colors is extremely high for the cell morphology and the localization of the virus.

Figure 12:
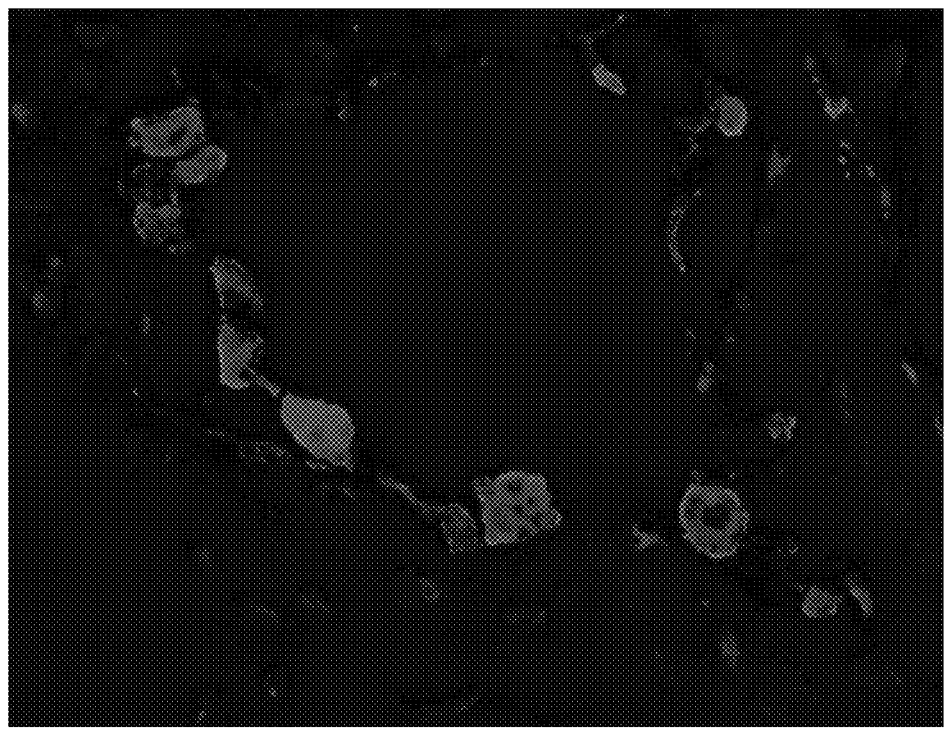

FIG. 12 is a stained cell image of lung alveolar structures of a patient deceased by COVID-19. The cells were imaged with nuclear localizing stains linked to fluorescence reporters. More specifically, the cells were stained using a blue-fluorescent DNA stain (e.g., DAPI) and a macrophage cell-identifying monoclonal antibody for CD163 (e.g., antiCD163 which is a macrophage-specific transmembrane glycoprotein) that contains a red fluorophore (e.g., Invitrogen Alexa Fluor 594). The cells were then imaged using an A1 HD25/A1R HD25 confocal microscope with dye-specific filter assessment. Cell nuclei and diffuse cell bodies are shown in blue (DAPI) while the macrophage-targeting Alexa-monoclonal antibody (anti-CD163) is shown in red. As those skilled in the art will appreciate, the specificity of these reporting colors is extremely high for the cell morphology and the localization of the CD206 marker glycoprotein.

Figure 13:
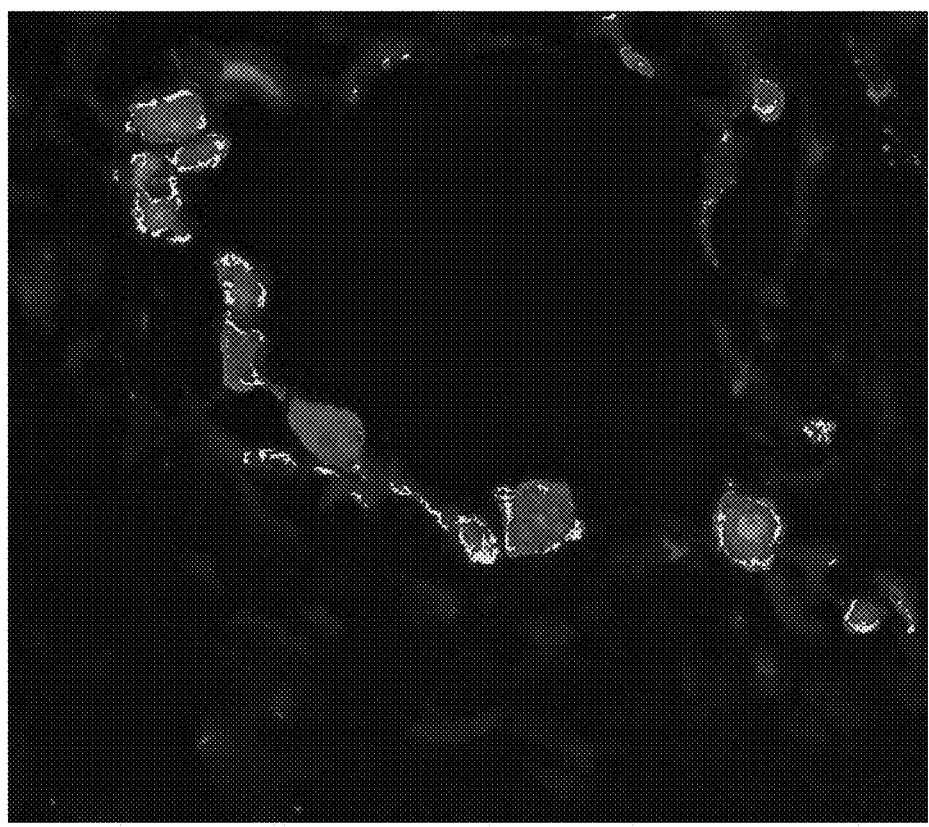

FIG. 13 is a merging of the images in FIGS. 11 and 12 to demonstrate the colocalization of the macrophage cell marker (CD163) and the SARS-2-Covid viral nucleocapsid protein (yellow when markers are colocalized). As those skilled in the art will appreciate, the tissue slices are exactly the same (FIGS. 11 and 12) and the merging of these markers is significant evidence of the specific localization of the infectious agent (SARS-2-covid) with the macrophage-specific marker CD163.

Collectively, FIG. 2 through FIG. 13 indicate that these are the only pulmonary cells (macrophages) in which the progression of disease in the lungs persists to late-stage disease. Notably, this unexpected finding makes such cells in the lungs and other tissues (such as liver and kidney tissues) targets for the agent described herein. Furthermore, these images indicate that diagnosis may be made by evaluating such tissue for the presence, non-presence, or presence in a predetermined amount, percentage, or the like of such expressing macrophages.

The compositions disclosed herein may be administered to a subject to prevent the acquisition of Covid-19. The subject may be exposed to these compositions prior to infection to prevent or ameliorate infection. Additionally, or alternatively, the compositions disclosed herein may be administered to a subject who is already exhibiting symptoms of Covid-19, to treat Covid-19 and/or the symptoms of Covid-19.

In certain embodiments, agents, compounds and/or compositions comprise tilmanocept (TIL, dextran 3-[(2-aminoethyl)thio]propyl 17-carboxy-10,13,16-tris(carboxymethyl)-8-oxo-4-thia-7,10,13,16-tetraazaheptadec-1-yl-3-[[2-[[1-imino-2-(D-mannopyranosylthio)-ethyl]amino]ethyl]-thio] propyl ether complexes), with or without afore-described moieties.

Compositions disclosed herein, such as tilmanocept and/or manocept along with their congeners, may be used as antivirals against Covid-19 family viruses. In certain embodiments, compositions described herein may be administered prior to conceiving a child to prevent the transmission of Covid-19, or other RNA viruses. In some embodiments, compositions described herein may be administered to males and/or females to prevent or reduce transmission of Covid-19, or other Corona family viruses.

Embodiments of tilmanocept as described herein can comprise therapeutic agents as described herein for curing, ameliorating, preventing, and/or treating Corona virus and/or the symptoms of Corona virus. In these embodiments, tilmanocept may or may not contain moieties as described above, or combinations of moieties such as $Cu^{2+}$ and hydroxychloroquine.

In certain embodiments, tilmanocept is administered to a patient to cure, ameliorate, prevent, kill, eliminate, and/or treat symptoms caused by Corona virus. To cure, ameliorate, prevent, and/or treat Corona virus, tilmanocept may be administered to a patient as described herein. In some embodiments, tilmanocept comprising a Corona or Covid virus therapeutic agent may be administered as a local intradermal injection. In other embodiments, tilmanocept comprising a Covid virus therapeutic agent may be administered intravenously or by inhalation.

Although the foregoing description is directed to the preferred embodiments of the invention, it is noted that other variations and modifications will be apparent to those skilled in the art and may be made without departing from the spirit or scope of the invention. Moreover, features described in connection with one embodiment of the invention may be used in conjunction with other embodiments, even if not explicitly stated above.

The invention is not limited in its application to the details of construction and the arrangement of components set forth in the following description or illustrated in the following drawings. The invention is capable of other embodiments and of being practiced or of being carried out in various ways.

Any embodiment of the present invention may include any of the features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

What is claimed is:

1. A method of treating RNA virus infections in a subject, said method comprising the steps of:

administering, to the subject afflicted with an RNA virus, a treatment dose of compound comprising a dextran backbone with a C-type lectin targeting moiety attached thereto, wherein the compound is devoid of any therapeutic agents attached to the dextran backbone, and wherein the treatment dose is between 5 milligrams and 30 grams; and delivering the compound to cells of the subject that comprise C-type lectin.

2. The method of claim 1, wherein the compound is administered to the patient in the form of a pharmaceutical composition comprising a therapeutically effective amount of the compound and a pharmaceutically acceptable carrier.

3. The method of claim 1, wherein the treatment dose is between 250 milligrams and 3 grams.

4. The method of claim 1, wherein the compound is administered by inhalation or transdermal entry.

5. The method of claim 1, wherein the compound is administered by injection intravenously, intradermally, or subcutaneously.

6. The method of claim 1, wherein:

the C-type lectin targeting moieties is attached to the dextran backbone; and the dextran backbone comprises a molecular weight ranging from about 16 kilodaltons to about 21 kilodaltons.

7. The method of claim 1, wherein:

the dextran backbone comprises a plurality of glucose residues; and

C-type lectin targeting moieties are attached to about 10 percent to about 50 percent of the glucose residues.

8. The method of claim 1, wherein the dextran backbone comprises at least one of tilmanocept and m-tilmanocept.

9. The method of claim 1, wherein the C-type lectin targeting moiety targets at least one of CD206, CD209, mincle, CD69, CD23, I-selectin, LOX-1, MBP, Dectin-1, NKG2D, and CLEC-2.

* * * * *